US011531025B2

(12) United States Patent
Guo

(10) Patent No.: US 11,531,025 B2
(45) Date of Patent: Dec. 20, 2022

(54) FORMATION AND USE OF EMBEDDED SOLUTIONS IN NANOSCALE MATERIALS

(71) Applicant: The Regents of the University of California, Oakland, CA (US)

(72) Inventor: Ting Guo, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 144 days.

(21) Appl. No.: 16/041,107

(22) Filed: Jul. 20, 2018

(65) Prior Publication Data

US 2018/0328921 A1 Nov. 15, 2018

Related U.S. Application Data

(63) Continuation of application No. PCT/US2017/014454, filed on Jan. 20, 2017.

(60) Provisional application No. 62/286,268, filed on Jan. 22, 2016.

(51) Int. Cl.
*G01N 33/542* (2006.01)
*G01N 23/223* (2006.01)

(52) U.S. Cl.
CPC ......... *G01N 33/542* (2013.01); *G01N 23/223* (2013.01)

(58) Field of Classification Search
None
See application file for complete search history.

(56) References Cited

U.S. PATENT DOCUMENTS

| | | |
|---|---|---|
| 2005/0064604 A1 | 3/2005 | Bohmann et al. |
| 2006/0067889 A1 | 3/2006 | Pallenberg et al. |
| 2007/0105176 A1* | 5/2007 | Ibey .................. C12Q 1/54 435/14 |
| 2008/0261202 A1 | 10/2008 | Baker et al. |
| 2010/0233726 A1 | 9/2010 | Tsien et al. |
| 2011/0275061 A1 | 11/2011 | Weidemaier et al. |
| 2013/0345391 A1 | 12/2013 | Knutson et al. |
| 2014/0162892 A1 | 6/2014 | Mir |
| 2014/0256059 A1 | 9/2014 | Geddes |
| 2015/0265706 A1 | 9/2015 | Vo-Dinh et al. |

FOREIGN PATENT DOCUMENTS

WO 2017/127759 A1 7/2017

OTHER PUBLICATIONS

Jiang et al. A chemically reactive Raman probe for ultrasensitively monitoring and imaging the in vivo generation of femtomolar oxidative species as induced by anti-tumor drugs in living cells. 2013 Chem. Commun. 49: 6647-6649. (Year: 2013).*

Guo, T., Nanoparticle Enhanced X-Ray Therapy. In ACS Annual Meeting Philadelphia, PA, Aug. 2004, 25 pages.
Amato et al., Monte Carlo Study of the Dose Enhancement Effect of Gold Nanoparticles During X-Ray Therapies and Evaluation of the Anti-Angiogenic Effect on Tumour Capillary Vessels, Journal of X-Ray Science and Technology, vol. 21, No. 2, 2013, pp. 237-247.
Anzai et al., ESR Measurement of Rapid Penetration of DMPO and DEPMPO Spin Traps Through Lipid Bilayer Membranes, Archives of Biochemistry and Biophysics, vol. 415, No. 2, Jul. 15, 2003, pp. 251-256.
Brun et al., Gold Nanoparticles Enhance the X-Ray-Induced Degradation of Human Centrin 2 Protein, Radiation Physics and Chemistry, vol. 78, No. 3, Mar. 2009, pp. 177-183.
Butterworth et al., Variation of Strand Break Yield for Plasmid DNA Irradiated with High-Z Metal Nanoparticles, BioOne Complete, Radiation Research, vol. 170, No. 3, Sep. 2008, pp. 381-387.
Carter et al., Nanoscale Energy Deposition by X-Ray Absorbing Nanostructures, The Journal of Physical Chemistry B Letters, vol. 111, No. 40, Oct. 11, 2007, pp. 11622-11625.
Chanana et al., Coating Matters: The Influence of Coating Materials on the Optical Properties of Gold Nanoparticles, Nanophotonics, vol. 1, No. 3-4, Dec. 2012, pp. 199-220.
Chen et al., Nanoscintillator-Mediated X-ray Inducible Photodynamic Therapy for In Vivo Cancer Treatment, Nano Lett., vol. 15, No. 4, Apr. 8, 2015, pp. 2249-2256.
Cheng et al., Chemical Enhancement by Nanomaterials Under X-Ray Irradiation, Journal of The American Chemical Society, vol. 134, No. 4, Jan. 19, 2012, pp. 1950-1953.
Cheng et al., Visible-Light-Assisted Degradation of Dye Pollutants over Fe(III)-Loaded Resin in the Presence of $H_2O_2$ at Neutral pH Values, Environmental Science & Technology, vol. 38, No. 5, Mar. 1, 2004, pp. 1569-1575.
Cho, S., Estimation of Tumour Dose Enhancement Due to Gold Nanoparticles During Typical Radiation Treatments: A Preliminary Monte Carlo Study, Physics in Medicine and Biology, vol. 50, Jul. 13, 2005, pp. N163-N173.
Davidson et al., An Example of X-ray Nanochemistry: SERS Investigation of Polymerization Enhanced by Nanostructures Under X-ray Irradiation, The Journal of Physical Chemistry Letters, vol. 3, No. 22, Oct. 2012, pp. 3271-3275.
Davidson et al., Average Physical Enhancement by Nanomaterials under X-Ray Irradiation, Journal of Physical Chemistry C, vol. 118, No. 51, Dec. 2, 2014, pp. 30221-30228.
Davidson et al., Multiplication Algorithm for Combined Physical and Chemical Enhancement of X-ray Effect by Nanomaterials, The Journal of Physical Chemistry, vol. 119, Jul. 30, 2015, pp. 19513-19519.

(Continued)

*Primary Examiner* — Jennifer Lamberski
(74) *Attorney, Agent, or Firm* — Kilpatrick Townsend & Stockton LLP

(57) ABSTRACT

Provided herein are methods and materials that allow targeting and imaging of interactions between probes and targets. In some embodiments, the probes include nanoscale materials with embedded solutions that can be used to measure physical enhancement by materials under X-ray irradiation. In some embodiments, the methods of the present invention include delivering a probe material to a target that can have a delivered donor material. In some embodiments, methods of the present invention include irradiating the target and determining an optical change in the probe characteristic of a physical enhancement.

20 Claims, 25 Drawing Sheets

(56) References Cited

OTHER PUBLICATIONS

Fernandez-Lopez et al., Highly Controlled Silica Coating of PEG-Capped Metal Nanoparticles and Preparation of SERS-Encoded Particles, Langmuir Article, vol. 25, No. 24, Dec. 15, 2009, pp. 13894-13899.

Foley et al., Enhanced Relaxation of Nanoparticle-Bound Supercoiled DNA in X-Ray Radiation, The Royal Society of Chemistry, Chem. Commun., vol. 25, Jul. 7, 2005, pp. 3192-3194.

Fortier et al., Covalently Bound Fluorescent Probes as Reporters for Hydroxyl Radical Penetration into Liposomal Membranes, Free Radical Biology & Medicine, vol. 46, No. 10, May 15, 2009, pp. 1376-1385.

Frens et al., Controlled Nucleation for the Regulation of the Particle Size in Monodisperse Gold Suspensions, Nature Physical Science, vol. 241, Jan. 1, 1973, pp. 20-22.

Gosetti et al., Identification of Sulforhodamine B Photodegradation Products Present in Nonpermanent Tattoos Bymicro Liquid Chromatography Coupled with Tandem High-Resolution Mass Spectrometry, Anal Bioanal Chem., vol. 407, No. 16, Jun. 2015, pp. 4649-4659.

Guidelli et al., Synthesis and Characterization of Silver/Alanine Nanocomposites for Radiation Detection in Medical Applications: The Influence of Particle Size on the Detection Properties, Nanoscale, vol. 4, No. 9, Apr. 28, 2012, pp. 2884-2893.

Guo et al., Enhanced X-Ray Attenuation Property of Dendrimer-Entrapped Gold Nanoparticles Complexed with Diatrizoic Acid, Journal of Materials Chemistry, vol. 21, No. 13, Mar. 2011, pp. 5120-5127.

Hainfeld et al., The Use of Gold Nanoparticles to Enhance Radiotherapy in Mice, Phys. Med. Bio., vol. 49, No. 18, Sep. 21, 2004, pp. N309-N315.

Jang et al., Controlled Supramolecular Assembly of Micelle-Like Gold Nanoparticles in PS-b-P2VP Diblock Copolymers via Hydrogen Bonding, Journal of the American Chemical Society, vol. 133, No. 42, Oct. 26, 2011, pp. 16986-16996.

Lee et al., Geometry Enhancement of Nanoscale Energy Deposition by X-Rays, The Journal of Physical Chemistry C, vol. 116, No. 20, Apr. 11, 2012, pp. 11292-11297.

McConnell et al., Tunable Wetting of Nanoparticle-Decorated Polymer Films, Langmuir Article, vol. 25, No. 18, Sep. 15, 2009, pp. 11014-11020.

McMahon et al., Energy Dependence of Gold Nanoparticle Radiosensitization in Plasmid DNA, The Journal of Physical Chemistry C, vol. 115, 2011, pp. 20160-20167.

Okada, Efficient Evaluation of Poly(oxyethylene) Complex Formation with Alkali-Metal Cations, Macromolecules, vol. 23, Sep. 1, 1990, pp. 4216-4219.

Sadtler et al., Spherical Ensembles of Gold Nanoparticles on Silica: Electrostatic and Size Effects, Chem. Commun., vol. 15, Aug. 7, 2002, pp. 1604-1605.

Sahoo, H., Forster Resonance Energy Transfer—A Spectroscopic Nanoruler: Principle and Applications, Journal of Photochemistry and Photobiology C: Photochemistry Reviews, vol. 12, No. 1, Mar. 2011, pp. 20-30.

Schmidt et al., Liposome Directed Growth of Calcium Phosphate Nanoshells, Adv. Mater. vol. 14, No. 7, Apr. 4, 2002, pp. 532-535.

Starkewolf et al., X-Ray Triggered Release of Doxorubicin from Nanoparticle Drug Carriers for Cancer Therapy, Chem. Commun., vol. 49, No. 25, Mar. 28, 2013, pp. 2545-2547.

Yang et al., Semiconductor Nanoparticles as Energy Mediators for Photosensitizer-Enhanced Radiotherapy, Int. J. Radiation Oncology Biol. Phys., vol. 72, No. 3, Nov. 1, 2008, pp. 633-635.

Yeo et al., Comparison of DOPA and DPPA Liposome Templates for the Synthesis of Calcium Phosphate Nanoshells, Science Direct, Ceramics International, vol. 38, No. 1, Jan. 2012, pp. 561-570.

Zhao et al., Photodegradation of Sulforhodamine-B Dye in Platinized Titania Dispersions under Visible Light Irradiation: Influence of Platinum as a Functional Co-catalyst, J. Phys. Chem. B, vol. 106, No. 19, Apr. 2002, pp. 5022-5028.

Zheng et al., Radiosensitization of DNA by Gold Nanoparticles Irradiated with High-Energy Electrons, BioOne Complete, vol. 169, No. 1, Jan. 2008, pp. 19-27.

* cited by examiner

FIG. 11C
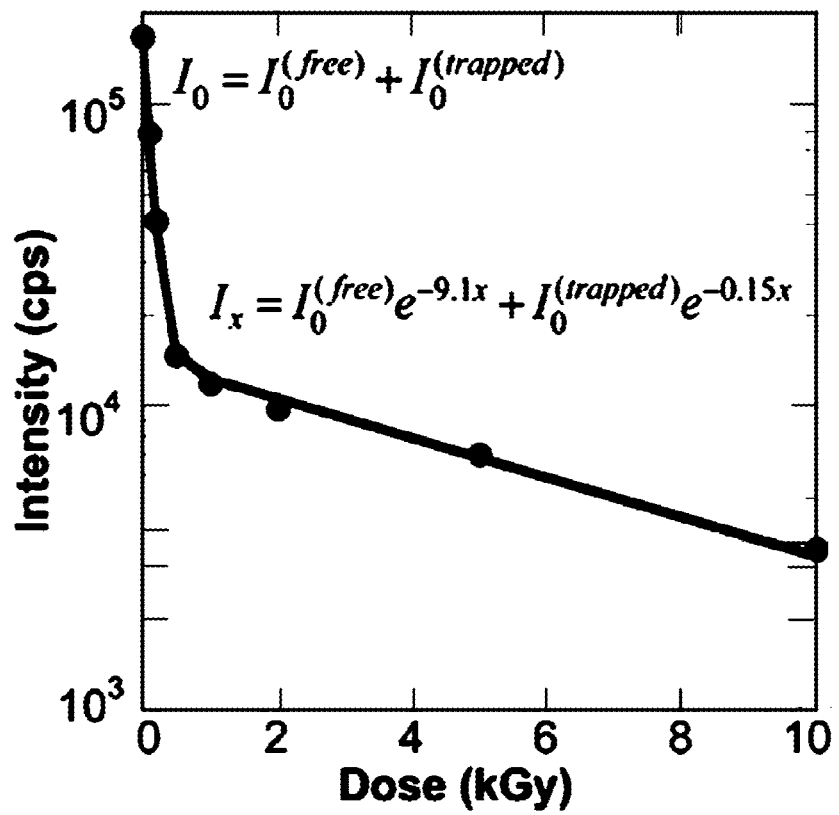
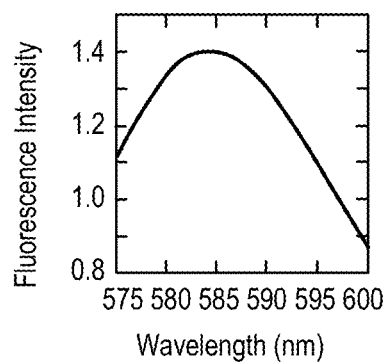
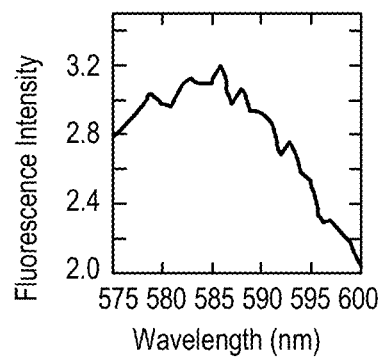

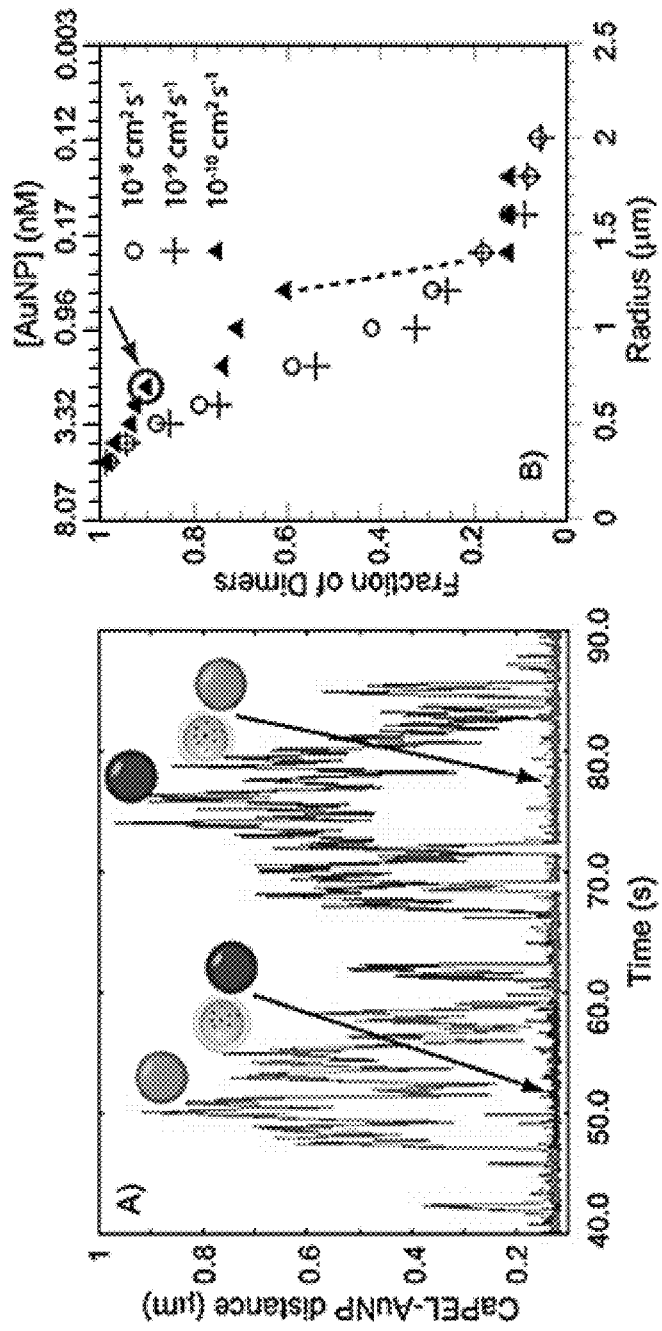

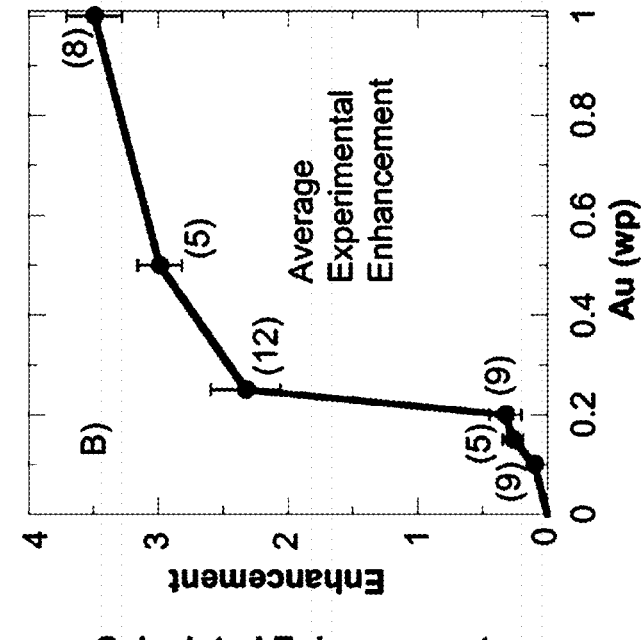
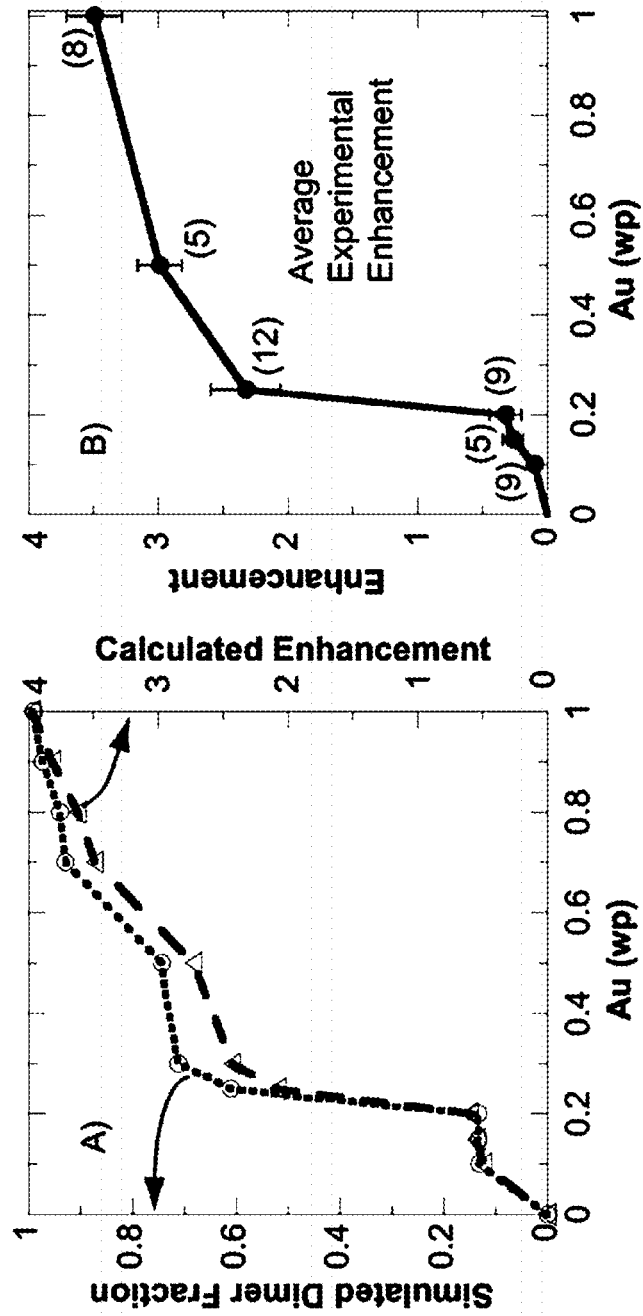
FIG. 18B
FIG. 18A

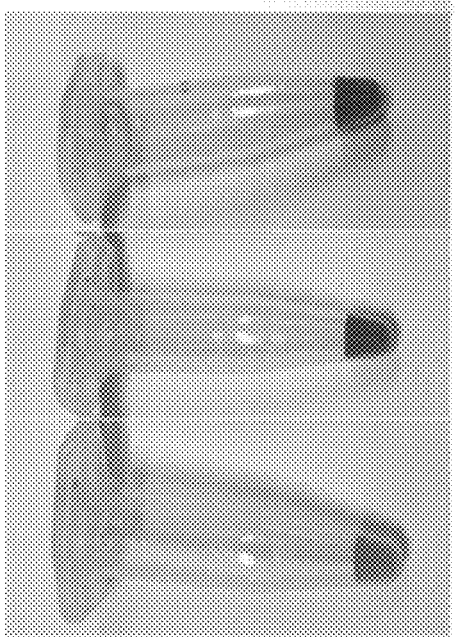
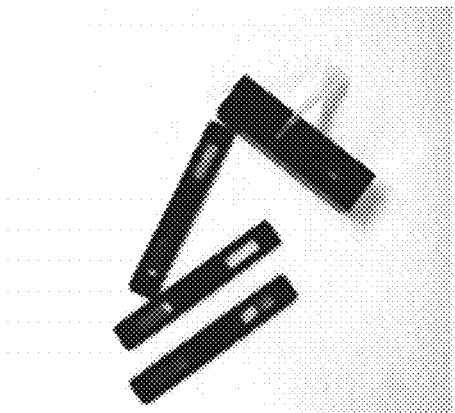
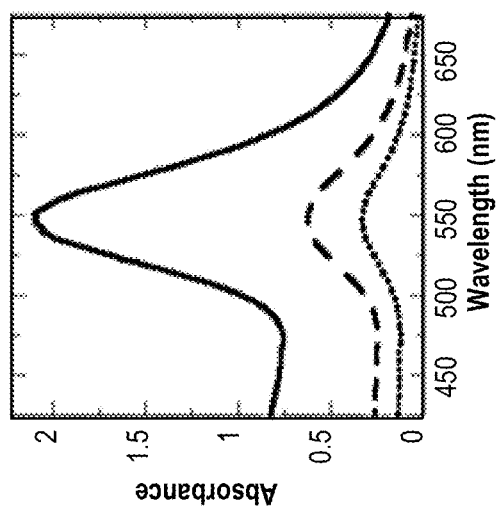
FIG. 19A
FIG. 19B
FIG. 19C

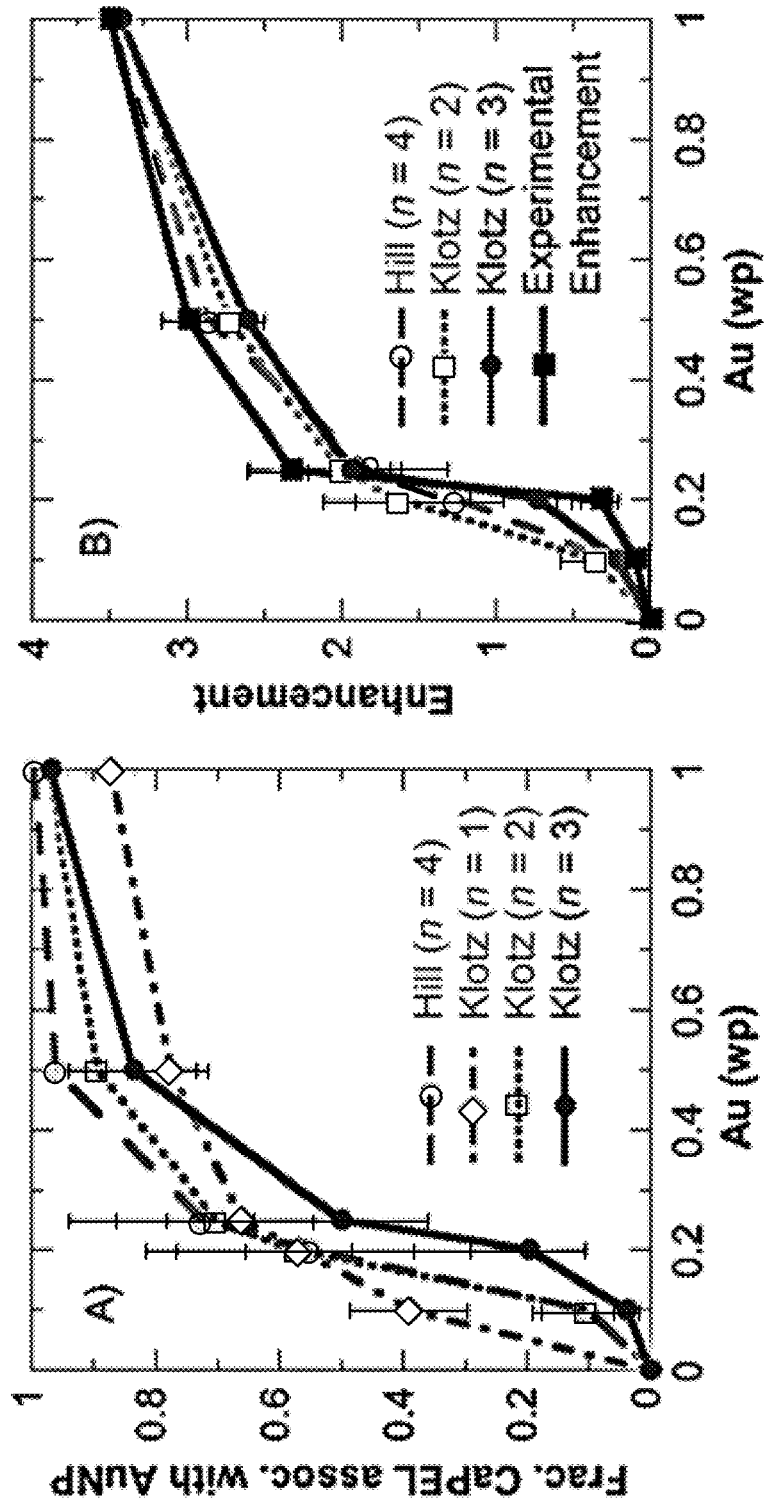

FORMATION AND USE OF EMBEDDED SOLUTIONS IN NANOSCALE MATERIALS

CROSS-REFERENCE TO RELATED APPLICATIONS

This application is a continuation of International Patent Application No. PCT/US2017/014454 filed Jan. 20, 2017, which claims the benefit of and priority to U.S. Provisional Application No. 62/286,268, filed Jan. 22, 2016, the disclosures of which are herein incorporated by reference in their entirety for all purposes.

STATEMENT AS TO RIGHTS TO INVENTIONS MADE UNDER FEDERALLY SPONSORED RESEARCH OR DEVELOPMENT

This invention was made with Government support under Grant No. CHE-1307529, awarded by the National Science Foundation. The government has certain rights in this invention.

BACKGROUND OF THE INVENTION

X-ray nanochemistry investigates how to use nanomaterials to enhance the effect of X-rays and how to use X-rays to drive previously un-encountered chemical reactions with the assistance of nanomaterials. Development of X-ray nanochemistry has been inspired by techniques such as nanoparticle enhanced X-ray therapy (NEXT) and has been accompanied by many advancements in the area of studying the interaction between nanomaterials and ionizing radiation. Applications of X-ray nanochemistry include but are not limited to cancer treatment and diagnostics, sensing, imaging of nanomaterials, fuel and chemical synthesis, and environmental studies. In order to explore and realize the full potential of X-ray nanochemistry, it is critical to identify, isolate, and optimize individual enhancement mechanisms.

Enhancement from adding nanomaterials is defined as the ratio of the signal detected by a probe with the nanomaterials in a medium to that of the medium alone. Such an enhancement originates from several sources and enhancements discovered to date include physical, chemical, and anti-enhancement. Physical enhancement (PE) derives from increased absorption of X-rays by the added nanomaterials and the resulting increase in energy deposition by electrons emitted from the X-ray absorbing nanomaterials in water if the nanomaterials are dissolved in water. PE can be further divided into at least two types, 1 and 2, or T1PE and T2PE. T1PE is an average effect caused by high energy electrons released from X-ray absorbing nanoparticles (hence the energy donor) and is independent of the location of nanomaterials because these energetic electrons traverse microns in water. T1PE can be as high as 1.0-1.5 fold in the whole volume of water per one weight percent (wp) of gold nanoparticles (AuNPs) uniformly dissolved in water. T2PE, on the other hand, is enabled by low energy electrons released from X-ray absorbing nanoparticles depositing energy within the nanometer vicinity of nanomaterials. As a result, T2PE occurs only near the surface of nanomaterials. The term "near" means the volume of interest lies 100 nm within the surface. Theoretically predicted T2PE, defined as the ratio of energy deposition with nanoparticles to without nanoparticles within a 5-nm thick shell surrounding spherical nanoparticles, can reach over 40 fold for individual 800-nm dia. AuNPs and over 200 fold for aggregated nanostructures. All contemporary publications showing enhanced energy deposition had measured the T1PE and there is no experimental demonstration of exclusive T2PE prior to this work.

SUMMARY OF THE INVENTION

In a first aspect, the invention provides a method of confirming a targeting operation. In some embodiments, the method comprises delivering a donor material to a target, delivering a probe to the target, irradiating the target, and determining an optical change in the probe to confirm that the donor material and probe reached the target. In some embodiments, the method further comprises functionalizing the donor material to seek the target, functionalizing the probe to conjugate with the donor material, and retrieving the probe subsequent to irradiating the target.

In some embodiments, retrieving the probe comprises delivering a solution to dislodge the probe from the donor material and extracting the probe from a living organism. In some instances, the target comprises cancerous tissue in the living organism. In other instances, extracting the probe comprises performing a blood draw. In particular instances, the solution comprises and elevated pH. In other instances, the solution is configured to sever the conjugation between the probe and the donor material. In some embodiments, the probe comprises dye molecules, and determining an optical change in the probe comprises destruction of the dye molecules In other embodiments, the donor material comprises at least one material selected form the group consisting of lanthanide oxide, hafnium oxide, tungsten oxide, platinum, gold, bismuth, and uranium (238). In some instances, the donor material comprises a nanomaterial having a diameter between about 25 nm and 1,000 nm.

In some embodiments, the probe comprises at least one material selected from the group consisting of $TiO_2$, ZnO, $Al_2O_3$, $SiO_2$, CaP, polystyrene, and poly N-isopropylacrylamide. In some instances, the probe further comprises at least one material selected from the group consisting of coumarin-3-carboxylic acid, 3'-(p aminophenyl) fluorescein or 2-[6-(4V-amino)phenoxy-3H-xanthen-3-on-9-yl] benzoic acid (APF), dihydroethidine (DHE), dihydrorhodamine, 4',5'-diaminofluorescein, sulforhodamine B, calcein, and fluorescein.

In some embodiments, the probe has a diameter between about 2 nm and 500 nm. In some instances, the probe has a diameter between about 5 nm and 100 nm.

In a second aspect, the invention provides a method of determining conjugation between a probe nanomaterial and a donor nanomaterial. In some embodiments, the method comprises functionalizing a donor nanomaterial to target a substance, delivering the donor nanomaterial to a location, functionalizing a probe nanomaterial to target the donor nanomaterial, delivering the probe nanomaterial to the location, irradiating the location, testing the probe nanomaterial to identify a change in optical characteristics, determining successful conjugation between the probe nanomaterial and the donor nanomaterial at the location, and based on determining successful conjugation, determining that the substance exists at the location.

Other objects, features, and advantages of the present invention will be apparent to one of skill in the art from the following detailed description.

BRIEF DESCRIPTION OF THE DRAWINGS

FIG. 5A shows a Cryo-TEM image of liposomes according to the present technology. FIG. 5B shows a TEM image of CaPELs (3-hour reaction time) according to the present technology. FIG. 5C illustrates DLS results of liposomes (solid line) and CaPELs (dashed line) according to the present technology. The average size of liposomes is 92 nm (DLS), and CaPELs are 130 nm (DLS) and 115 nm (TEM). FIG. 5D shows a TEM image of AuNPs according to the present technology.

FIG. 7A shows experimental results of using different nanomaterials to test the enhancement mechanisms for the 45 nm and 240 nm AuNPs according to the present technology. FIG. 7B shows the results of enhancement measurements using AuNP@SiO$_2$ and filtered X-rays according to the present technology.

FIG. 8A illustrates the distance dependency of XIET for a 90-nm AuNP next to a CaPEL according to the present technology. FIG. 8B illustrates the simulated enhancement for one, two and three AuNPs of different diameters in contact with a CaPEL according to the present technology.

FIGS. 11A-11D demonstrate the use of CaPELs loaded with SRB to detect XIET. FIG. 11A depicts some of the decomposition products of SRB due to ROS. FIG. 11B shows raw fluorescence signal of SRB in CaPELs exposed to increasing X-ray dose. Decomposition of SRB into non-fluorescent products causes decrease in fluorescence intensity with increased X-ray dose. Peak fluorescence signal at 585 nm was used for data analysis. FIG. 11C shows X-ray degradation of SRB dye in a dialyzed CaPEL sample containing both free as well as encapsulated SRB (circles) and the mathematical fit. The spectra in the inset show fluorescence signals of SRB in CaPELs prior to (i.e., 0 kGy) and after exposure to 10 kGy dose of X-ray radiation. FIG. 11D shows degradation of free SRB in solution at two different SRB concentrations of 1 mM (circles) and 0.5 µM (squares) along with their mathematical fits.

FIG. 13A shows CaPELs at a quenching time of 0.25 hr and shell thickness of 7+/−2 nm. FIG. 13B shows CaPELs at a quenching time of 3 hours and shell thickness of 14+/−3 nm. FIG. 13C shows CaPELs at a quenching time of 20 hours and shell thickness of 50+/−6 nm.

FIGS. 17A and 17B show theoretical modeling results. FIG. 17A presents the results of BD modeling where the green (denoted "(G)") and red (denoted "(R)") plots correspond to the distances between the centers of the CaPEL (100 nm dia. plus a 15-nm CaP shell) and any one of the two AuNPs (100 nm dia. plus a 15-nm PEG shell). The CaPEL is considered to bind to AuNPs when the distance between the particle centers falls below 130 nm. FIG. 17B shows the fraction of the total modeling time in which the CaPEL binds to one AuNP. Three diffusion coefficients were used, as given here. A dotted line is drawn for visual guidance for the lowest diffusion coefficient case. The circled data point represents FIG. 17A.

FIGS. 18A and 18B compares simulated and experimental results. FIG. 18A shows predicted enhancements based on BD modeling results and an enhancement simulation. Both dimer percentage (short dashed line) and the resulting enhancements (long dashed line) are shown. FIG. 18B shows experimentally measured enhancement results with different concentrations of AuNPs. The results show a significant jump at 0.25 wp AuNPs on top of a gentle slope enhancement, largely agreeing with the theoretical modeling and enhancement simulation results shown in FIG. 18A. The numbers in parentheses indicate the number of repeats at each AuNP concentration.

FIGS. 19A-19C shows UV-Vis results. FIG. 19A shows three different concentrations (0.1, 0.25, and 1.0 wp, from left to right) of 90 nm AuNP samples in Eppendorf tubes. FIG. 19B shows the thin cuvettes. FIG. 19C shows the UV-Vis spectra of 0.1 wp (dotted line), 0.5 wp (dashed line), and 1.0 wp (solid line) of 90 nm AuNPs, which are almost identical to each other, indicating no aggregations of AuNPs.

FIGS. 20A and 20B depict Kotz equations and a comparison of experimental and simulated results. FIG. 20A shows the results of three individual Klotz equations (n=1, 2, and 3) with selected equilibrium constants (for n=1, $K_1$=0.1-0.01; for n=2, $K_1$=1×10$^{-5}$-5×10$^{-5}$, $K_2$=10-70; and for n=3, $K_1$=1×10$^{-4}$, $K_2$=0.1-0.5, $K_3$=1-10) and Hill equation (with n=4±0.4 and $K_d$=1×10$^{-5}$-5×10$^{-5}$). FIG. 20B shows the comparison between the experimental enhancement data and the average predicted enhancement results based on Klotz equation (for n=2 & 3 with different equilibrium constants) and the Hill equation.

DETAILED DESCRIPTION OF THE INVENTION

I. Introduction

Figure 1:
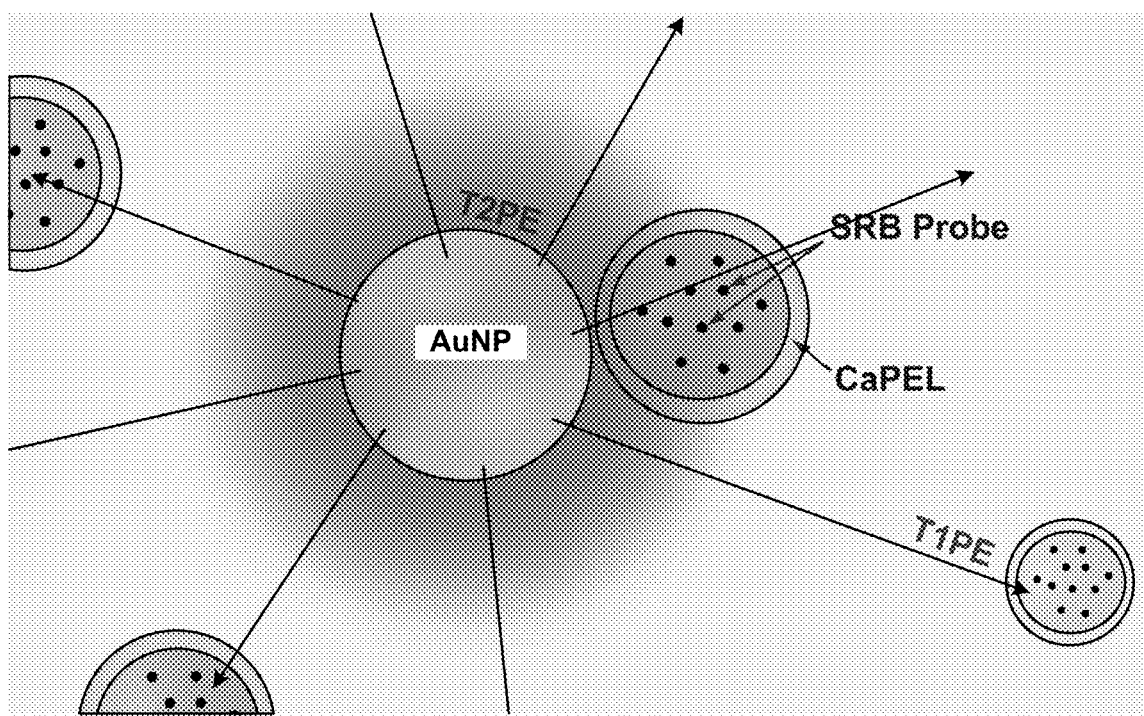
FIG. 1 illustrates the X-ray Induced Energy Transfer (XIET) Type I Physical Enhancement and Type II Physical Enhancement processes discussed in the context of the present technology.

The present technology is related to targeting and imaging interactions between probes and their targets. The probes may include nanoscale materials with embedded solutions that may be used to measure physical enhancement by materials under X-ray irradiation. The physical enhancement and the efficiency of the enhancement, as described in detail below, may be indicative of a properly located target.

Because it is nearly impossible to directly probe electrons in water or other media with nanometer spatial resolution, enhancement is usually probed with a chemical reaction, with an energy deposition process such as scintillation, or with any event that can detect the energy released from the X-ray absorbing nanomaterials. However, when a chemical reaction such as hydroxylation or polymerization is used as dosimetric reactions to probe PE, the reaction is subjected to further catalytic modifications by nanomaterials and reactive oxygen species (ROS) in solution. Such catalytic processes are called chemical enhancement (CE). In one example, as much as 30 fold CE was found with polymerization of aniline by nanomaterials under X-ray irradiation. It should be pointed out that CE does not need the nanomaterials to strongly absorb X-rays because CE utilizes the ROS generated in the medium such as water to catalytically activate nanomaterials. Hence the existence of CE does not depend on PE as long as nanomaterials are catalytically active. In the presence of large quantities of nanomaterials, there is another process called anti-enhancement (AE) that could occur due to scavenging of ROS by the nanomaterials, either by their surfactants or surface.

From the above discussion it is apparent that T2PE from nanostructures is desirable due to its high enhancement. Previously T2PE or similar concepts were proposed and calculated, and T2PE was also measured in the presence of other types of enhancement because DNA probe molecules were not isolated from CE or AE and only low enhancements were detected. In order to isolate and detect exclusive T2PE, up to three conditions may be required. The first condition is that the probes may be confined in the T2PE region. As a result, nanoscale probes may be required. Otherwise, even though T2PE can be one to two orders of magnitude higher than T1PE, the integrated T2PE contribution may be still much smaller than T1PE if probes are uniformly distributed in the whole volume of the sample because the fraction of volume in which T2PE dominates is extremely small compared with that of T1PE. The second condition may be to avoid or isolate CE and AE from T2PE, which is possible because AE or CE occurs at the surface whereas the T2PE occurs near the surface of nanomaterials. The term "at" means to be in contact with the surface and "near" means to be within nanometers of the surface. The third condition may be to ensure reactive species generated outside the T2PE region cannot diffuse into T2PE region if the enhancement measurement is based on probes stored in the T2PE region reacting with ROS generated in water. This means the nanoscale probes may be characterized by walls impenetrable by certain ROS but that are thin enough for high energy electrons to pass.

In the new experimental platform created by this technology, T2PE may be probed based on energy transfer between nanomaterial energy donors and acceptors under X-ray irradiation, a process the inventor has dubbed X-ray Induced Energy Transfer or XIET (homophone of "excite").

The original definition of T2PE of energy flowing from the X-ray absorbing nanoparticle to a volume within a thin shell around a spherical nanoparticle was conveniently devised for theoretically calculating T2PE. Because the nanoscale acceptors are used here, a more practical approach is needed so the enhancement can be accurately calculated and represented, and T2PE may be redefined in the framework of energy transfer between two nanomaterials of any shape. Specifically, the strongly X-ray absorbing AuNPs as well as several other nanostructures were synthesized as energy donors that generate T2PE. One of the energy acceptors synthesized by the present technology to measure XIET (T2PE) is calcium phosphate enclosed liposomes (CaPELs) with sulforhodamine B (SRB) aqueous solution trapped inside. Because liposomes are permeable to many ROS, the liposome exterior surface was coated with calcium phosphate (CaP) after SRB probe molecules were trapped inside the liposomes. The XIET(T1PE) and XIET(T2PE) processes are illustrated in FIG. 1 which shows an exemplary process where radiation interacts with the nanomaterials to produce electrons mainly from the AuNP donor. These electrons then interact with water inside spherical acceptors, such as CaPELs, next to the AuNP to generate ROS within the CaPELs, some of which react with SRB to cause it to break down and become non-fluorescent. As shown in FIG. 1, it is natural to use the description of energy transfer from donors to acceptors when AuNPs and CaPELs are used. With CaPELs or other nanoscale acceptors, the enhancement may depend on the dimensions of the CaPELs, but may not depend on the previously defined volume of spherical shells around the AuNP for obtaining the original T2PE.

The establishment of XIET and use of nanoscale probes/acceptors isolates the probing molecules from the environment so that SRB is not in contact with the enhancing nanomaterials (i.e., AuNPs), therefore eliminating CE and AE. Because the acceptors can be near the surface of the AuNP and not uniformly distributed in the whole sample volume, T2PE is not overwhelmed by T1PE. The term "near" again means the acceptors are within nanometers of the donors. In addition, CaP shell thickness can be tuned to completely stop permeation of ROS from passing the wall of the nanoscale probes while still allowing electrons to pass. Therefore, these particular, designed nanoscale probes satisfy the three conditions mentioned above.

II. Detailed Description of the Embodiments

The described donor and acceptor nanomaterials may be used for a range of uses including identifying a target by determining whether the donor materials are present in a location. The present methods utilize dye molecule aqueous solutions embedded in nanoscale cavities that can be used to detect energy transfer caused from other materials nearby while both types of materials are under X-ray irradiation. The amount of X-ray induced energy transferred from the other material to the nanoscale cavity can be determined by the degree to which the dye molecules are damaged. Because the amount of energy transfer may depend to a large extent on the distance between the two materials, this method can be used to measure the distance between the two types of materials with a spatial resolution greater than 10 nm. Also because X-rays (20 to 160 keV) are highly penetrating, it is possible to use these nanoscale probes and X-ray induced energy transfer enabled methods to investigate hidden dynamics such as drug targeting or particle aggregation in the body or plants or other opaque and large objects. Additionally, because the resolution may have a majority or complete dependence on the distance between the two materials and not the absolute position of the X-ray absorbing material, this technique may not lose its resolution power even when the latter moves, such as in the situation where the materials are within a living body.

Figure 2:
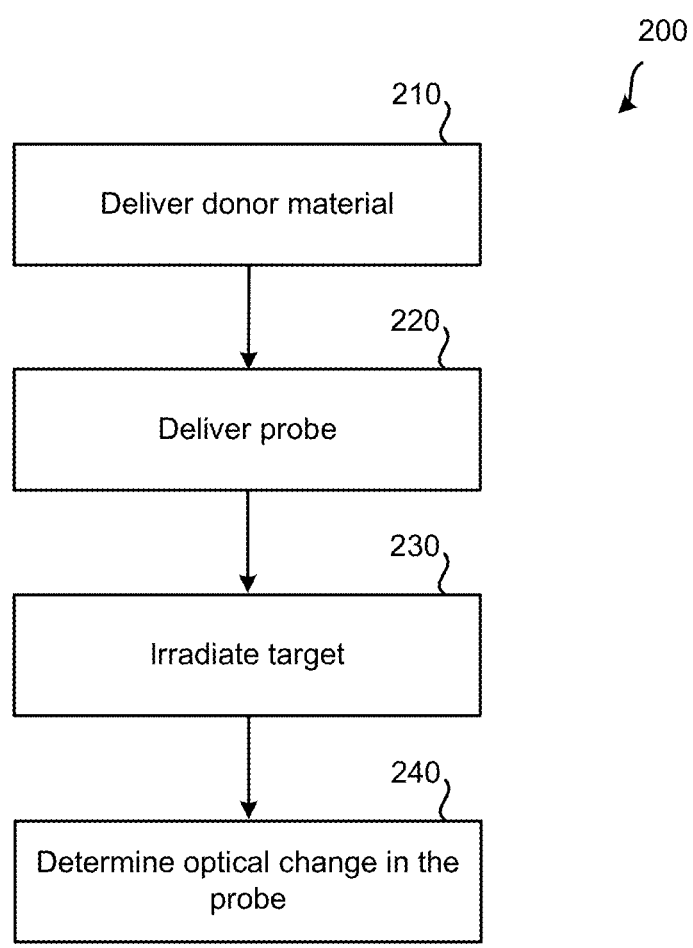
FIG. 2 illustrates a method of confirming a targeting operation according to the present technology.

Turning to FIG. 2 is illustrated a method 200 of confirming a targeting operation according to the present technology. The method may include delivering a donor material to a target at operation 210. The delivery may be injection, diffusion, inhalation, or may include any other delivery that may introduce the donor material to the target host. The target may be a known target or a sought target, such as cancerous cells, for example. The target may also be a sought target in a known location in embodiments, such as searching for cancer cells in a particular organ, for example. The method 200 may provide a determination or confirmation of whether the target exists. The method may also include delivering a probe to the target at operation 220. The probe delivery may be by a similar or different delivery than the donor delivery, and may also be by injection in embodiments.

The methods may include irradiating the target at operation 230. In embodiments this operation may involve irradiating the location where the target is sought, such as irradiating the general location of an organ. The irradiation may be by X-ray in embodiments and may be delivered by any X-ray source, and may also be by microwave, gamma rays, high energy electrons, or other radiative sources. Various doses of irradiation energy may be used to irradiate the target or location in embodiments. The irradiation dose may be low dose or high dose, and may be between 0.1 and 100 Gy. The dose may be up to or about 1 Gy, up to or about 5 Gy, up to or about 10 Gy, between about 2 Gy and about 50 Gy, between about 10 Gy and about 75 Gy, between about 20 Gy and about 50 Gy, or any other range of values between about 0.1 Gy and about 100 Gy. The irradiation dose may also be at least about 100 Gy, at least about 200 Gy, at least about 300 Gy, at least about 400 Gy, at least about 500 Gy, at least about 600 Gy, at least about 700 Gy, at least about 800 Gy, at least about 900 Gy, at least about 1000 Gy, at least about 1100 Gy, at least about 1200 Gy, at least about 1300 Gy, at least about 1400 Gy, or at least about 1500 Gy. The irradiation dose may be less than about 250 Gy, between about 250 Gy and about 1000 Gy, between about 500 Gy and about 1500 Gy, or between about 700 Gy and 1200 Gy.

The methods may include determining an optical change in the probe at operation 240. This optical change may be as a result of the irradiation, and may be induced or caused by T2PE from the donor material as previously explained. Identifying the optical change in the probe may confirm that the donor material and probe reached the target.

In embodiments, the donor material may be a nanoparticle, and may be a gold-containing nanoparticle. The donor material may be characterized by a spherical shape in embodiments, but may be other shapes as well. The donor material may also include or consist of lanthanide oxide; hafnium oxide, tungsten oxide, platinum, bismuth, or uranium (238) in embodiments. The donor material may have a range of sizes from about 25 nm to about 1,000 nm. The donor material may have a size from about 30 nm to about 500 nm, or at least about 40 nm, at least about 50 nm, at least about 60 nm, at least about 70 nm, at least about 80 nm, at least about 90 nm, at least about 100 nm, at least about 125 nm, at least about 150 nm, at least about 200 nm, at least about 250 nm, at least about 300 nm, at least about 350 nm, at least about 400 nm, or at least about 450 nm. In additional embodiments the donor material may be an organism, or tissue within an organism, and may be an organ such as a liver, lung, or tumor tissue, for example.

The probe may include a number of materials, and may include an acceptor material and a probing material in embodiments. The acceptor material may include $TiO_2$, ZnO, $Al_2O_3$, $SiO_2$, CaP, polystyrene, or poly N-isopropylacrylamide in embodiments. The probing material may be molecules incorporated with or embedded within the acceptor material. The probing material may include Coumarin-3-carboxylic acid, 3'-(p aminophenyl) fluorescein or 2-[6-(4V-amino)phenoxy-3H-xanthen-3-on-9-yl] benzoic acid (APF), dihydroethidine (DHE), dihydrorhodamine, and 4',5'-diaminofluorescein, sulforhodamine B, calcein and fluorescein. The probe may be of a variety of sizes, and may have a diameter from about 1 nm to about 1000 nm in embodiments, and may be between about 2 nm and about 500 nm, or between about 5 nm and about 100 nm. The acceptor size may be selected based on the donor materials used. For example, larger donor materials may allow for larger probe materials. For implantable materials, up to about 1000 nm or more is reasonable, and the size may also be less than or about 1000 nm, less than or about 750 nm, less than or about 500 nm, less than or about 200 nm, less than or about 100 nm, less than or about 90 nm, less than or about 80 nm, less than or about 70 nm, less than or about 60 nm, less than or about 50 nm, less than or about 40 nm, less than or about 30 nm, less than or about 20 nm, less than or about 10 nm, or between about 1 nm and 10 nm. The acceptor material may be characterized by a spherical shape, a cubic shape, a cylindrical shape, or other shapes in embodiments. The acceptor material may be a hollow shell in which the probing material has been trapped. In some embodiments, the probing material comprises a single particle. In other embodiments, the probing material comprises a plurality of particles. In particular embodiments, the probing material comprises a single particle contained within a hollow acceptor material shell. In still other embodiments, the probing material comprises a plurality of particles that are contained within a hollow acceptor material shell. The trapped probing material may include dye molecules in aqueous solution. The thickness of the acceptor shell may be between about 1 nm and about 100 nm, between about 5 nm and about 50 nm, between about 1 nm and about 30 nm, less than or about 30 nm, less than or about 25 nm, less than or about 20 nm, less than or about 15 nm, or less than or about 10 nm. The size of the probe material may be constrained in embodiments. For example, the probe may be of a certain size so that it is capable of sensing energy deposited, but small enough so that it does not weaken T2PE.

As explained further in the examples below, the efficiency of the energy transfer from the donor material to the probe may identify the distance between the particles. As explained below, there may be an exponential drop in efficiency of the transfer as the distance between the donor material and probe increases. Hence, if the probe is outside of a certain distance from the donor material, degradation of the probing material may be reduced or eliminated, and optical changes in the probe may not be realized, or may be recognized at a rate indicative of low T2PE, or greater distance from the donor material. Conversely, if the probe is within a particular distance of the donor material upon irradiation, energy transfer efficiency will increase along with probing material degradation. The optical change due to this degradation can be measured as explained below, and thus a distance between the probe and donor material may be confirmed within a distance of a few dozen nanometers or less, such as up to about 10 nm, up to about 20 nm, up to about 30 nm, up to about 40 nm, up to about 50 nm, or more.

For the example including sulforhodamine B in aqueous solution, this material can be damaged by X-ray irradiation and the response may be linear over a large dose range. Additionally, high concentrations of sulforhodamine B molecules can be trapped in calcium phosphate enclaved liposomes, for example, as well as other materials. Formation of this nanomaterial may produce a probe to detect ionization radiation including X-rays and electrons that can deposit energy inside the nanoscale cavity. The detection may be useful when the nanoscale cavities are close to the strongly X-ray absorbing materials such as heavy metal nanoparticles, including gold or lead nanoparticles, for example, or aggregates of these and other particles discussed above. The close vicinity of the nanoscale cavity to the heavy metal materials may provide increased energy deposition in the cavities over those which are away from the materials, and the increased deposition can be recorded and measured. The outcome of the measurement may reveal how close the nanoscale cavities have been to heavy metal materials.

In operation, these examples may be the detection of dynamics of nanoparticle interaction under conditions that may be too difficult to identify for other existing imaging methods. For this exemplary combination, the concentration of gold nanoparticles may be high and the samples may be opaque, thick pastes to the naked eyes. The nanoscale cavity probes may be mixed with these gold nanoparticles. The PEGylated gold nanoparticles may be attracted to the calcium ions on the surface of nanoscale cavities. However, this attraction force or energy may be weak and only at very high concentrations of gold nanoparticles may the two types of nanomaterials stay together to form heterodimers for the majority of the duration of measurement time. Because the gold nanoparticles are highly X-ray absorbing, whereas the nanoscale cavities are not, the gold nanoparticles will absorb X-rays and the absorption ionizes gold atoms to produce electrons, some of which escape the nanoparticles. Some of the escaped electrons enter the nanoscale cavity, depositing energy when the electrons interact with water in the cavity that is maintaining the probing material, such as SRB. The process is defined as X-ray induced energy transfer or XIET. The efficiency of this energy deposition in the nanoscale cavity may be highly dependent on the distance between the gold nanoparticles and the calcium phosphate enclaved liposomes. For many nanoparticles, the energy transfer may reduce from maximum at zero distance to less than 10% at 50 nm, and in some cases to 10% in 20 nm. Therefore, it is possible to determine the distance between the gold nanoparticles and calcium phosphate enclaved liposomes with a spatial resolution better than 10 nm.

Figure 3:
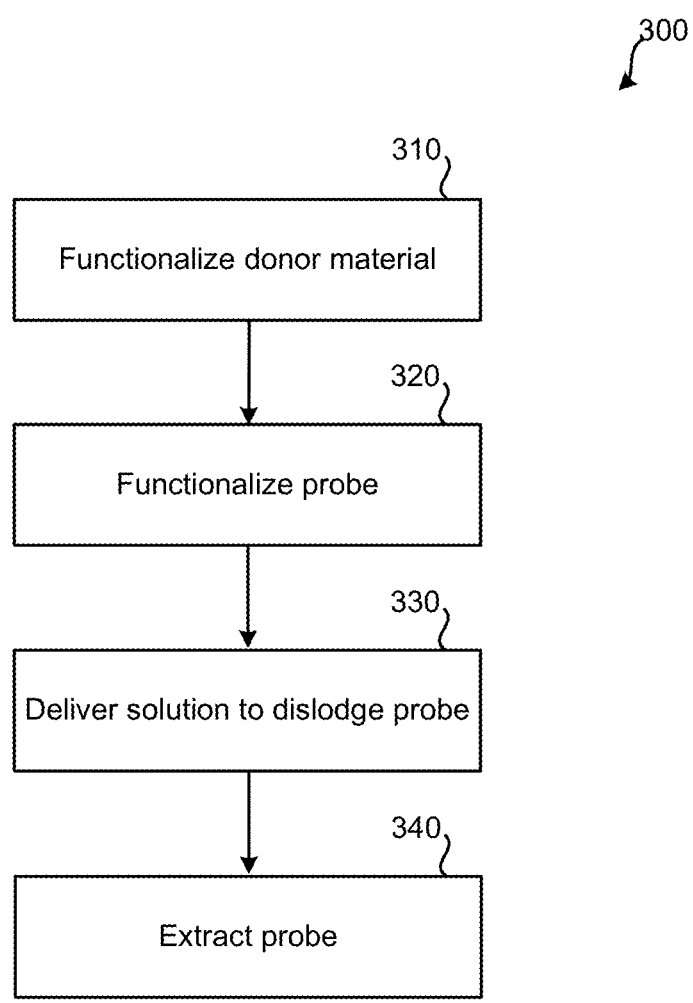
FIG. 3 illustrates optional operations that may be included in a method of confirming a targeting operation according to the present technology.

FIG. 3 illustrates optional operations 300 that may be included in the method 200. Any one or more of the optional operations may be included in the method 200. For example, optional operation 310 may be used in the method 200, and may include functionalizing the donor material to seek the target. For example, the target may be an organ, type of tissue, type of cell, or any other material that may be targeted. As one non-limiting example, cancer cells may often have abnormally high levels of epidermal growth factor receptor protein on the cellular surface. This protein or other materials indicative of cancerous cells may be targeted by functionalizing the donor material with ligands, such as peptides, antibodies, small-molecule inhibitors, as well as or with polyethylene glycol, RNA, DNA, surfactants, or a number of other materials that may target the cancerous cells. The functionalized donor material may then couple, link, bond, or be associated with the cancerous cells upon delivery. In embodiments, the donor material may also be functionalized to attract or allow the probe to target the donor material, and may be functionalized with any of the previously discussed materials.

Optional operation 320 may be used in the method 200, and may include functionalizing the probe to conjugate with the donor material. The materials used in the functionalizing of the probe may include materials that seek heavy metals, such as may be used in the donor material, or may be materials previously described that will attract the probe to the donor material. The conjugation may be a direct link or bond between the materials or functional moieties, but may also be an association based on electrostatic or other forces between the materials. As one non-limiting example, RNA aptamers may be included on the acceptor and a virus protein such as hemagglutinin (HA tag) may be included on the donor, which can have a number of different targeting agents such as peptide, folic acid or anti-EGFR on it to seek the target, which may be a tumor cell, for example. Upon sufficient X-ray irradiation, the aptamer may be broken, similar to a DNA strand break, and the enhancement may recorded with the acceptor by the radiation. After releasing from the conjugation, the acceptor may be collected and examined optically to determine the enhancement. If the enhancement is high, then the acceptor was likely very close to the donor. Although if it was low, the probe may not have been sufficiently close to the donor.

As another example, the donor material may have a number of thiol ligands on the surface. Maleimide ligands can then be coupled with the probes or acceptor material. Upon mixing, the two functional groups may covalently bond. Additionally, either the thiol or maleimide group can be linked to the donor or acceptor through a DNA strand. Then upon irradiating with a sufficient dose of X-rays, the DNA strand will be broken, and the acceptor may be released for optical detection. Accordingly, in embodiments, the donor material and probe material may be delivered simultaneously towards the target, and may be conjugated prior to delivery.

In another example, a magnetic core (>20 nm in diameter) can be put in the middle of the donor. The core may be paramagnetic. A few very small magnetic nanoparticles (~10 nm diameter) may be coated onto the surface of the acceptor. When a magnetic field is applied (100 to 1000 gauss), the small nanoparticles, which may be superparamagnetic, are attracted to the large magnetic particle in the core. X-ray irradiation can be applied during this period of time. Afterwards the external magnetic field may be removed, and the small magnetic nanoparticles on the surface of the acceptor become less attracted to the large magnetic core in the donor because the small nanoparticles are no longer magnetic after the removal of the external magnetic field. This may result in the departure of the acceptor from the donor, which may allow testers to measure their optical properties. Many other examples of both conjugating and severing the probe material from the donor material may be used, as would be understood to be encompassed by the present technology as well.

The linking or conjugation between the donor material and the probe may be confirmed prior to delivery, as well as that the probe will target the donor material. Thus, delivery of the probe to a host having the donor material is likely to have the conjugation occur. Continuing the previous example, if the donor material is functionalized to target the protein epidermal growth factor receptor indicative of cancerous cells, a relatively small amount of donor material, such as functionalized gold nanoparticles, may be delivered to the body in search of these cancerous cells in a particular organ, such as the lungs or liver for example, as well as breast tissue among a number of other examples. The functionalized probe may then be delivered, which may naturally seek out the donor material, and conjugate with that material. If the donor material has attached to or associated with cancer cells at the determined location, and irradiation energy is delivered causing XIET to degrade the probing material, the degradation can be confirmed, which also may confirm that the cancerous cells are in residence at the irradiated location.

Put another way, functionalizing the donor material and probe may allow both passive and active targeting. In the previous example, a concern of lung cancer may have been raised, and thus the targeting operation is performed to seek out cancerous cells in the lungs. If there are no cancerous cells, then the donor material—functionalized to target those cells specifically—would not link or associate with tissue of the lungs, and would travel freely elsewhere in the body. Once the probes are delivered, they would also travel past the lungs, and irradiation energy directed to the lung region would not cause XIET between the donor materials and probes that are not there. Upon retrieval of the probes, testing may show that optical characteristics have not changed as a result of XIET, and confirmation may be obtained that cancerous cells may not be located in the lungs. Conversely, if the donor material had connected with lung tissue exhibiting cancerous characteristics towards which the donor material had been functionalized, the functionalized probe would have conjugated with the donor material. After irradiation, XIET would occur, and could be confirmed upon retrieval and testing of the probe. This may allow confirmation that cancerous cells did reside in the lung tissue. It is to be understood that this example may be extended to encompass any other type of targeting utilizing this method both for alternative organs or locations, as well as alternative materials to be targeted. It is additionally to be understood that a donor material may include a plurality of donor materials, and a probe, may include a plurality of probes.

An advantage of the present technology is that a minimal amount of donor material, which may pose health hazards, may be delivered to the target. Especially because the material may travel elsewhere, there is a risk of damage to healthy cells or tissue. For example, if instead of the probe of the present technology a CT scan were used to identify the location of the functionalized donor material, a great amount of donor material may be required, such as upwards of one percent of gold, which can be overwhelming in a human system. The present technology, however, may allow a minimal amount of gold, for example, to be introduced because it can be tested at such a small distance from the particles, such as about 10 nm as previously described. Additionally, a smaller dose of radiation may be delivered at the exact location to be tested. In the examples discussed below, the inventors determined that the energy transfer experiences a jump when the concentration of gold nanoparticles is greater than a fraction of nanomolar. This jump may be explained as a sudden increase in the percentage of each calcium phosphate enclaved liposome attaching to at least one gold nanoparticle. As a result, the dynamic interaction information may be retrieved between these two types of nanoparticles. Below this threshold concentration, many calcium phosphate enclaved liposomes may not have gold nanoparticles attached to them, reducing the XIET effect.

Retrieval of the probe may be performed in a number of ways. In alternative embodiments, however, testing of the degradation may also be performed in situ. Optional operation 330 may be performed with method 200, and may include delivering a solution that is configured to dislodge the probe from the donor material. This may effectively perform a rinse to wash out the probes, which may then be tested for optical effect. Additionally, the donor material may remain at the target site, such as with a tumor, for example. The solution may include a slightly higher or lower pH which may break, sever, or reduce the association, connection, or conjugation between the probe and the donor material. For example, a solution with a pH of about 8.0-8.5 may be delivered to sever the connection between the two materials. The solution may be delivered in any number of ways including injection, inhalation, diffusion, or any other delivery that would introduce the solution to the donor material and probe. In embodiments, as explained above, the irradiation may also sever the conjugation or link between the probe and donor material.

Once the probes have been released, they may enter the bloodstream, for example, and can be sensibly detected in the veins, for example. In embodiments, in optional operation 340, which may be performed in method 200, the probes may be extracted from a living organism. For example, extracting the probe may include a blood draw. The collected probes may be tested optically to determine amount of degradation of the probing material, which may be a dye. The optical change in the probe may be a detected destruction of the dye molecules. The optical testing may be performed in situ or ex situ in embodiments. The probing materials described above include a number of available probing materials including dyes that may be used in the present technology. Each dye may have a peak that may be detected, and thus a dye working at about 800 nm can be safely checked in situ. Dyes may be chosen that have minimal absorption by biological samples, such as if their peak is within the water window, for example. These dyes may have very narrow peaks, which may be easily detected in testing. This may then be utilized as explained below to confirm whether the probes were at the target having the donor materials, or within a very narrow margin from the donor materials such as about 10 nm or less, up to about 20 nm, up to about 30 nm, up to about 40 nm, or up to about 50 nm.

The resolution of the present technology can be relatively equated to about 10 nm at a distance from the target of about 10 cm. This is roughly equivalent to locating an object of a few feet on the ground from a satellite orbiting the earth. Conventional testing methods including MRI, ultrasonic, and CT all have many orders of magnitude lower spatial resolution compared to the present technology. For hidden conditions, such as in situ measurements or detection, the present technology is superior to these conventional technologies. The present technology may also benefit from additional technologies including scanning focusing of X-ray devices, geometry enhancement, chemical enhancement, and enhancement algorithms. It may be possible to use a scanning focusing device to deliver a high dose of irradiation energy at a location, and then the nanocavity probes can be used to monitor the dose profile at that location. It may be also possible to deliver targeting nanomaterials to a tumor occupying the isocenter that is irradiated with the scanning focusing device, and then send in the probes to confirm the docking of the targeting nanomaterials. Geometry enhancement and chemical enhancement can be used to make the probes more sensitive.

It should be understood that materials described herein may be useful in many other types of applications including, but not limited to, medical applications, biological and chemical location determination, drug delivery systems and any other suitable application where a the described probe materials may be useful.

III. Examples

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1. Formation and Use of Nanoscale Probes

Introduction

A nanoscale probe of calcium phosphate enclosed liposomes filled with sulforhodamine B (SRB) aqueous solution was synthesized and the degradation of SRB in the probes was used to measure the enhanced energy deposition within the nanoscale probes after mixing them with PEGylated gold nanoparticles under X-ray irradiation. The enhancement was measured as a function of the gold nanoparticle concentration, and the results showed a surprising jump at 0.46 nM of gold nanoparticles with a steep slope of 42 fold per one weight percentage ($wp^{-1}$) of gold in water superimposed on a gentle 1 fold $wp^{-1}$ slope. Theoretical simulations revealed that the jump was caused by the previously proposed type 2 physical enhancement (T2PE) exerted from a single 90-nm gold nanoparticle on a contacting nanoscale probe and the gentler slope by type 1 physical enhancement (T1PE) was caused by the rest of gold nanoparticles hundreds of nanometer or farther away. The jump is equivalent to a 2-fold absolute enhancement for each nanoscale probe. This assignment also suggests that T1PE and T2PE obey the addition algorithm. The use of nanoscale probes creates a framework of X-ray induced energy transfer in which both T1PE and T2PE can be understood as energy transfer from gold nanoparticle donors to nanoscale probe acceptors. It will be appreciated that the calcium phosphate enclosed liposomes filled with SRB may be substituted throughout this example with a variety of other materials and dyes.

Materials and Methods

Figure 4:
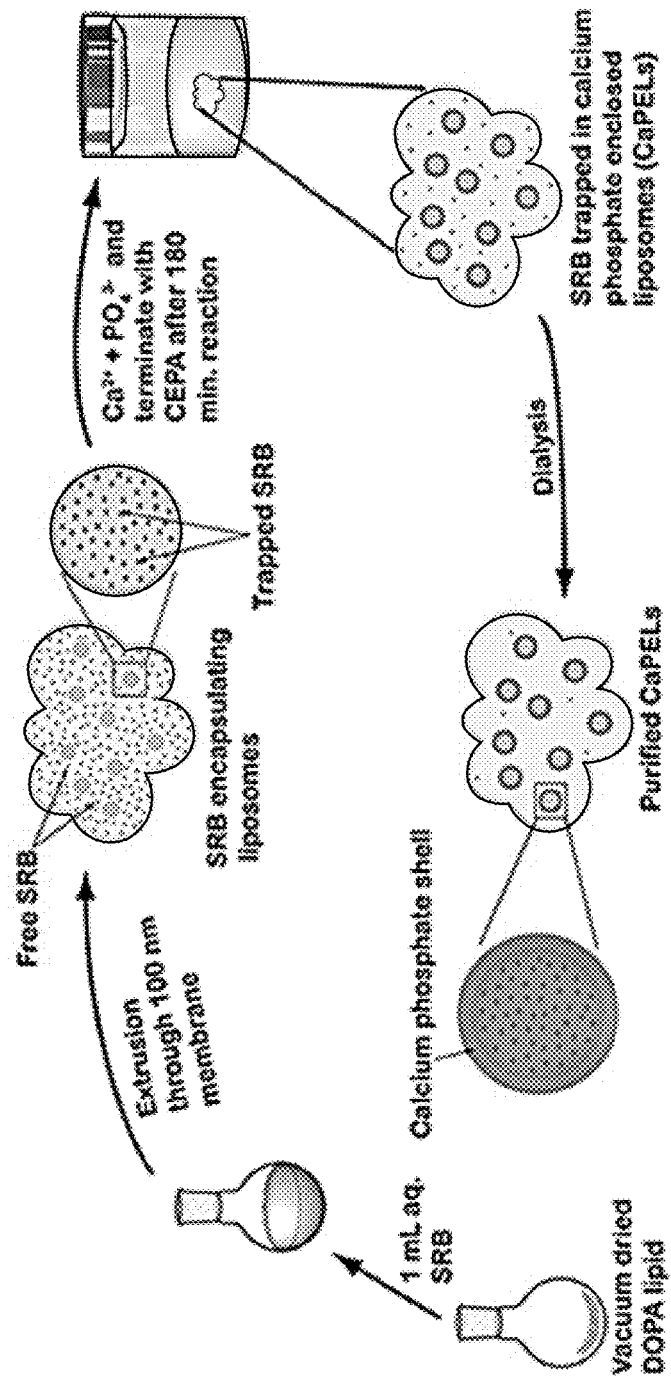
FIG. 4 illustrates the synthetic steps to make CaPELs, from lipids to coating CaP layers onto liposomes.

The chemicals and materials used or synthesized as well as the experimental procedures are described in more detail below in the Supplementary Information section of this example. Briefly, AuNPs, AuNP@SiO$_2$ and other nanomaterials were made and used in the measurements. FIG. 4 illustrates the synthetic steps to make CaPELs, from lipids to coating CaP layers onto liposomes. Dynamic light scattering (DLS), TEM, cryo-TEM and Nanoparticle Tracking Analysis (NTA) employing NanoSight (NS300, Malvern) were used to characterize the samples. Theoretical simulations based on Monte-Carlo method were performed to estimate the enhancement. The synthesis of CaPELs illustrated in FIG. 4 includes several operations. SRB molecules were incubated with lipids to make SRB embedded liposomes, over which a CaP shell was coated. Dialysis was done to the samples to get the final product in which there were still free SRB in the solution outside the CaPELs.

Figure 10:
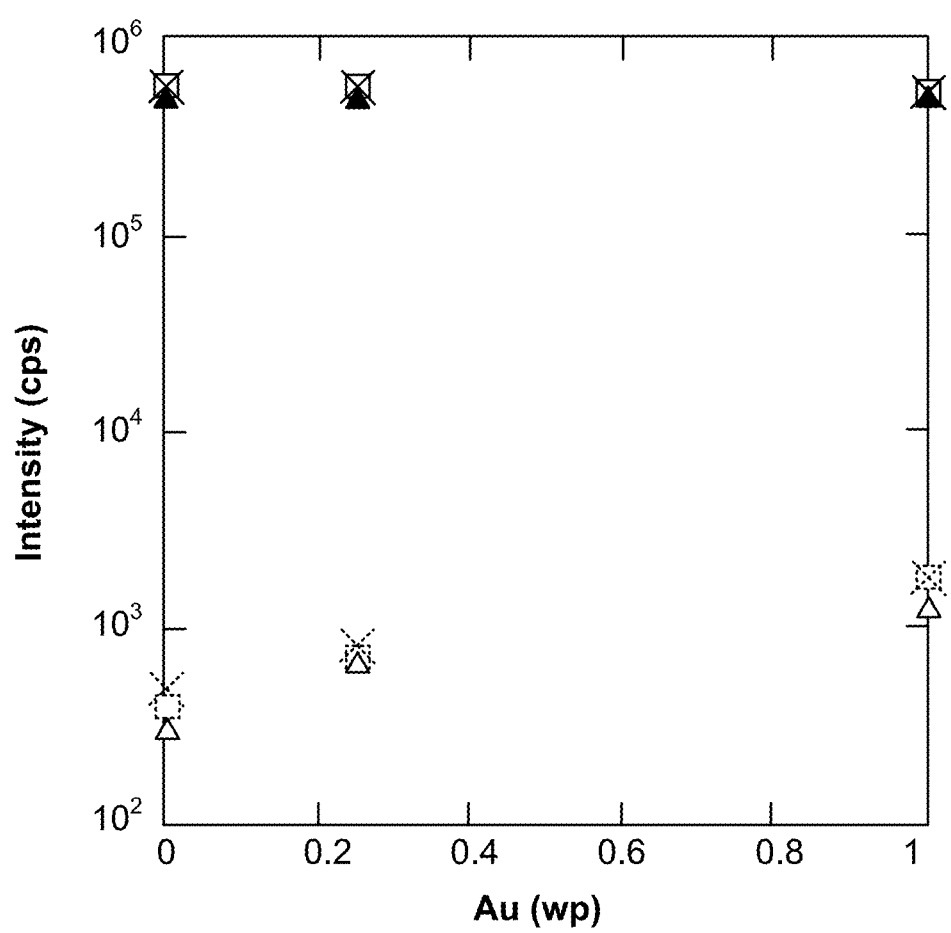
FIG. 10 shows the fluorescence of an aqueous solution of SRB (0.3 µM) before (top triangles) and after 1.2 kGy of X-ray irradiation (bottom triangles), illustrating the effect of anti-enhancement.

SRB was found in this study to be one of the most suitable probes among many dye molecules tested for enhancement measurement, although many other suitable probes may be used. The mechanism of using SRB to detect enhancement is through ROS reacting with and damaging SRB molecules to render them non-fluorescent. The damage of SRB was calibrated in this work and the results are shown in FIG. 10. These results were then used to calculate T2PE by AuNPs under X-ray irradiation. Therefore, this method may not directly measure energy deposition but infer it from SRB damage. SRB in water were damaged via reacting with ROS generated in water under X-ray irradiation. For 0.5 μM SRB in water, the damage rate constant was 7.0 $(kGy)^{-1}$. For 1 mM the rate of damage was about 0.15 $(kGy)^{-1}$ This dependency is caused by fixed amounts of ROS produced per unit of radiation; therefore higher concentrations of SRB have lower rates of damage. Damage of free SRB in the presence of AuNPs was also measured and the results are shown in FIG. 11, showing approximately 40% anti-enhancement (AE) per 1 wp of 90-nm AuNPs. For SRB in liposomes, because OH radicals can easily penetrate liposomes, the damage rate constant was close to that in pure water. Adding a thick layer of CaP outside liposomes stopped diffusion of OH radicals. Damage of SRB in CaPEL samples by X-rays also showed two decay rates: A fast component similar to the low concentration SRB outside CaPELs and a slow component close to that of 1 mM SRB inside CaPELs. Even with dialysis, the amount of SRB in the fast component was about 91% of the total SRB, assuming all SRB fluoresces equally. The average concentration including SRB inside and outside CaPELs after dialysis was 125 nM. Two ways were used to reduce the amount of free SRB in CaPEL samples. The first was chemical etching with Fenton's reagent and the second was pre-irradiation with X-rays. The free SRB amount was reduced to 50% of the trapped SRB after chemical etching. After irradiation of 200 Gy, over 70% of the 91% free SRB were damaged and became non-fluorescent. Unless specified, all the samples were irradiated for 1000 Gy after pre-irradiating the samples for 200 Gy.

Figure 6:
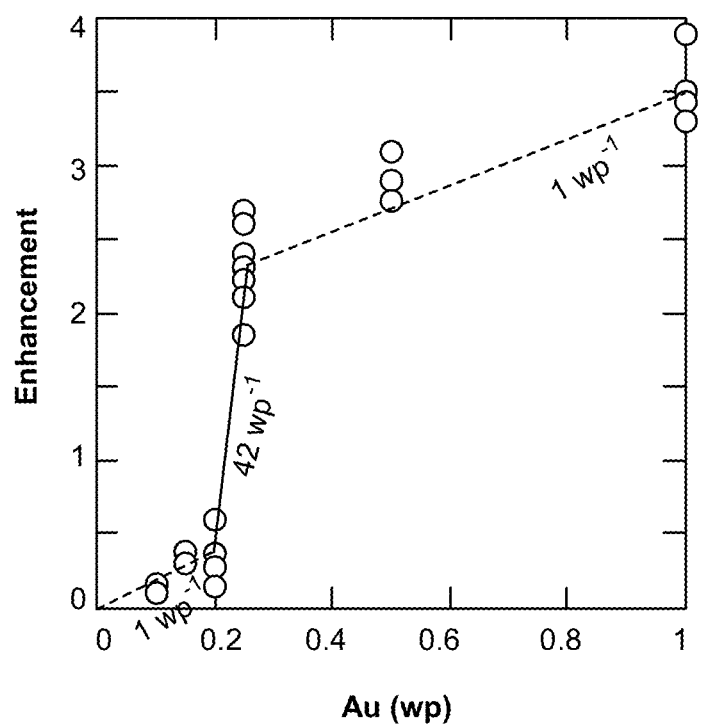
FIG. 6 illustrates enhancement measurement results as a function of concentration of AuNPs according to the present technology.

The procedure to calculate enhancement is detailed further below in the Supplementary Information section of this example. Briefly, the damage of SRB occurred at two rates. The outside SRB was damaged at a rate of 7-10 $kGy^{-1}$ and inside at approximately 0.1-0.2 $kGy^{-1}$ if there were no AuNPs. If AuNPs were added, more damage occurred to SRB inside CaPELs and the second rate constant was higher due to T1PE and T2PE. However, the fast rate constant was lower due to AE. For AuNP concentrations below 1.0 wp, AE contribution was below 10% and the results were largely the same as shown in FIGS. 6 and 7. For greater concentrations of AuNPs, whose data was not shown here, one must consider AE when calculating T2PE.

Figure 12:
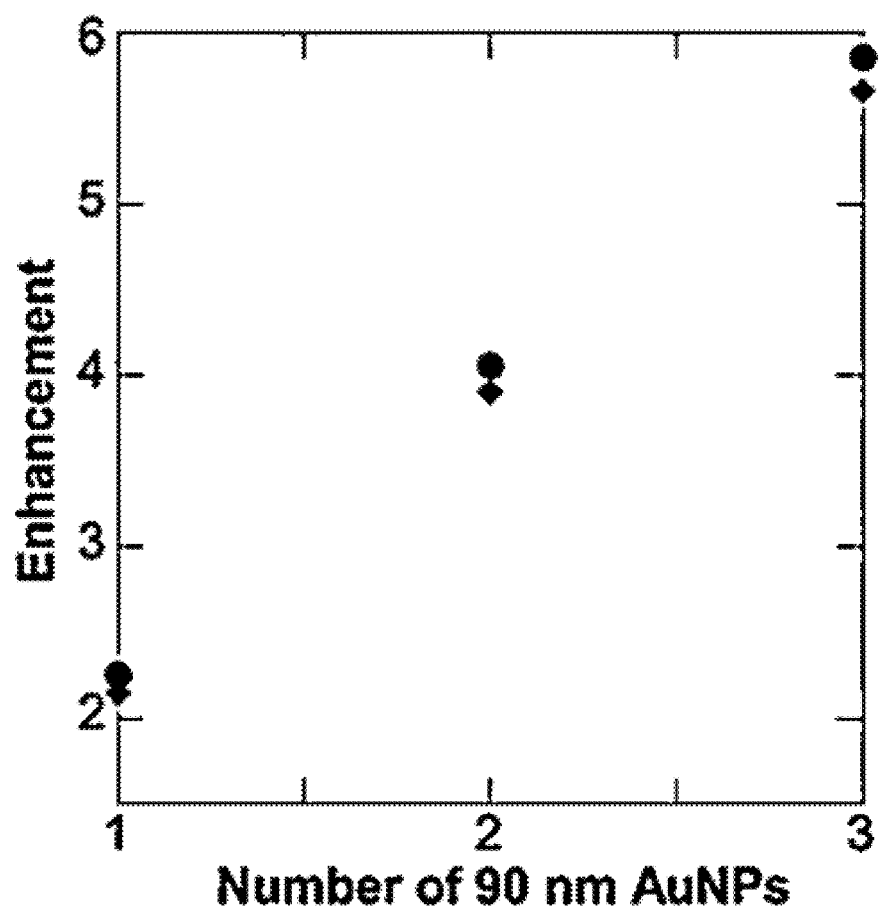
FIG. 12 shows the theoretical enhancement obtained for irradiation with 30 keV X-rays (circles). The theoretical average enhancement obtained on irradiation with an X-ray spectrum (10-100 keV X-rays) (diamonds) is shown for comparison.

The enhancement simulation method was based on a reported Monte-Carlo method and the details are given below in the Supplementary Information section of this example. Briefly, energy deposition in a specified volume was calculated based on electrons emitted from X-ray absorbing nanoparticles going through the interested volume. The calculated enhancement was corrected with reference to a unity relative enhancement or zero absolute enhancement by the deposition from the surrounding water without the nanoparticles. The enhancement was simulated using an X-ray spectrum covering 10 to 100 keV as well as by single X-ray energy at 30 keV. The two simulation results were nearly identical and the comparison results are shown in FIG. 12. Unless explicitly stated, 33-keV single photon energy was used in all the simulations here.

Results

Figure 5:
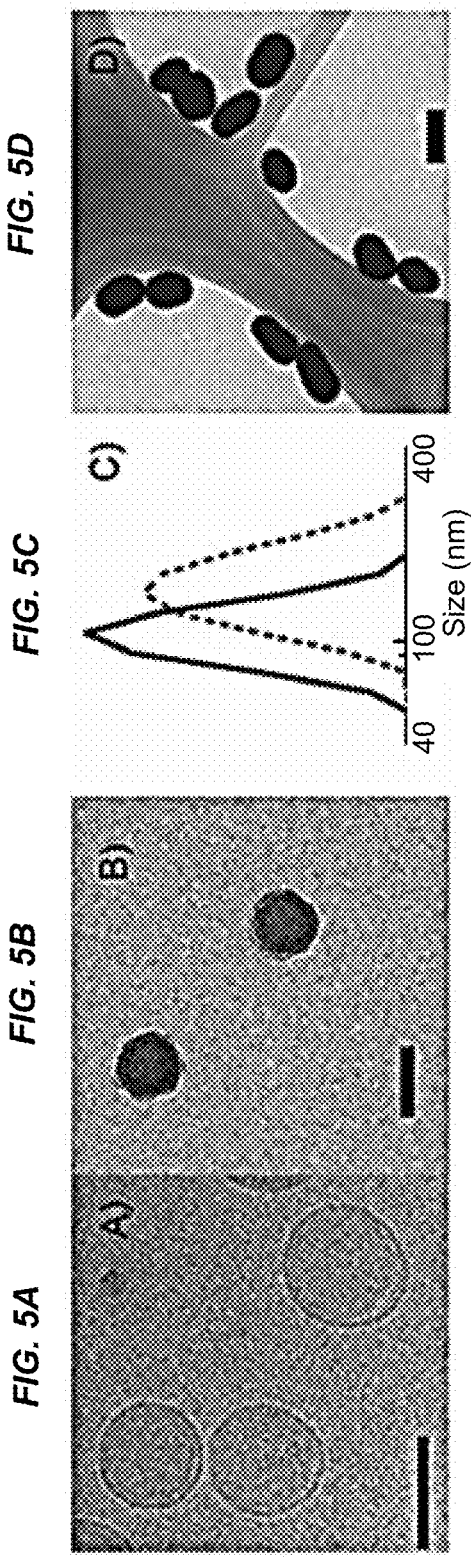
FIGS. 5A-5D illustrate various nanomaterials associated with the present technology.

The experimental results of SRB trapping CaPELs are shown in FIG. 5 and Table 1.

TABLE 1

Sizes and concentrations of AuNPs and CaPELs used

| | Size (nm) | | | | | Concentration | | |
|---|---|---|---|---|---|---|---|---|
| | PEG-AuNPs | Liposomes | CaPELs | CaP shell | CaPEL ID | Au-ions (wp) | PEG-AuNPs (nM) | CaPELs (nM) |
| DLS[a] | 98 ± 12 | 105 ± 10 | 130 ± 18 | 15 ± 2.5 | 100 ± 18.2 | | | |
| TEM[b] | 90 ± 8 | 106 ± 2.5[d] | 115 ± 12 | 15 ± 1.4 | 79 ± 8 | | | |
| NTA[c] | 76.9 ± 1.6 | | 97.7 ± 1.4 | | 67.7 ± 2.9[e] | 1 | 3.3 | 0.023[g] |
| AA[f] | | | | | | 1 | 2.3 | |

For the table above: (a) denotes dynamic light scattering (DLS), (b) denotes transmission electron microscopy (TEM), (c) denotes nanoparticle tracking analysis (NTA), (d) denotes cryo-TEM, (e) denotes results were obtained by subtracting CaP shell (DLS) from CaPELs (NTA; 68 nm ID (inner diameter) was used for calculations of CaPELs), (f) denotes the concentration of PEGylated AuNPs was calculated using the size of AuNPs measured with TEM and the amount of Au determined with atomic absorption (AA) spectroscopy, and (g) denotes that if a 15% yield of liposome formation from lipids was assumed, then the concentration should be 24 pM and was found to be 23 pM by NTA. The ratio of AuNP to CaPEL concentrations was 100:1 for 1.0 wp AuNPs mixed with the stock CaPEL aqueous solution. At 0.10 wp AuNPs, the ratio was 10:1.

Experimental results of enhancement measurements are shown in FIG. 6, which displays the enhanced degradation of SRB in terms of their fluorescence yield in CaPELs as a function of concentration of 90-nm AuNPs from 0.1 wp to 1.0 wp. The enhancement increased as AuNP concentration increased, following a slope of approximately 1 $wp^{-1}$ over the entire concentration range with a significant jump over the 0.2 to 0.25 wp span. A 0.2 wp corresponds to 0.46 nM for 90 nm AuNPs, and the ratio of CaPELs to AuNPs at this AuNP concentration was 1:20. The enhancement jump at 0.2/0.25 wp was equal to an enhancement increase of 2.1 fold over a 0.05-wp change in Au in water and was equivalent to a 42 $wp^{-1}$ enhancement, far exceeding the slope of the highest reported T1PE of 1 fold $wp^{-1}$. Because the gentle slope was close to the literature reported values of T1PE, and there was a weak attraction between PEG and $Ca^{2+}$ (25) the jump at 0.2/0.25 wp shown in FIG. 6 was likely caused by T2PE. Theoretical simulations confirmed this speculation.

Figure 7A:
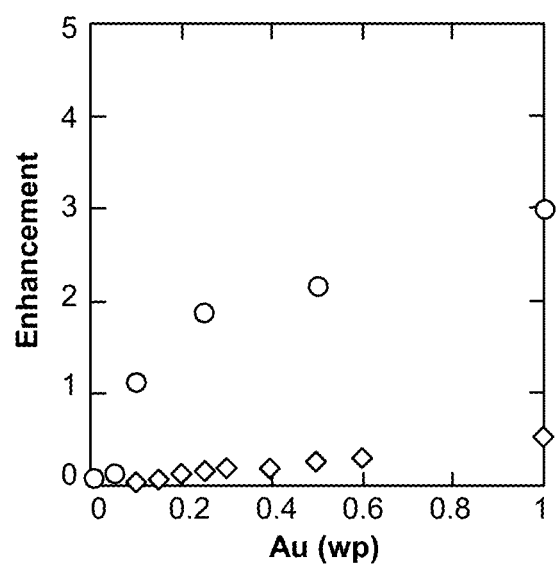
FIGS. 7A and 7B illustrate experimental results pertaining to use of the present technology.
Figure 7B:
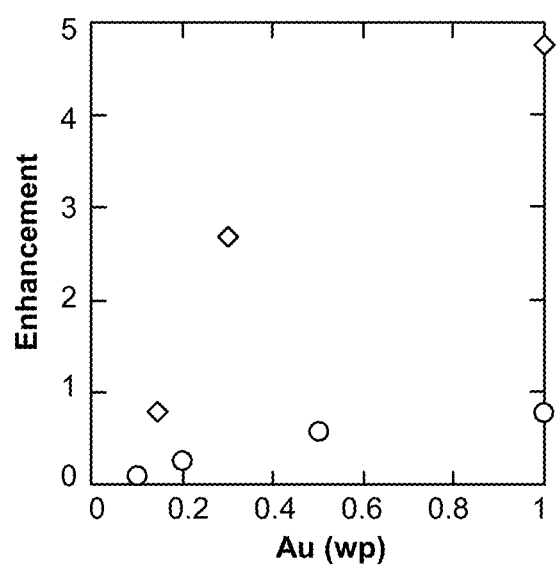
Figure 13:
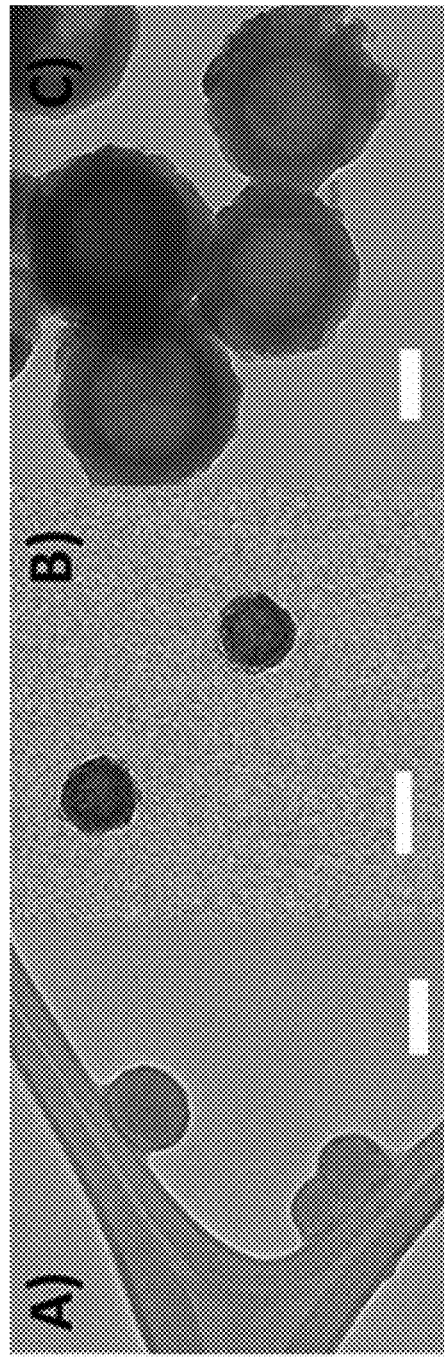
FIGS. 13A-C show TEM images of CaPELs at three reaction quenching times and shell thicknesses (based on TEM). Scale bars=100 nm.
Figure 14:
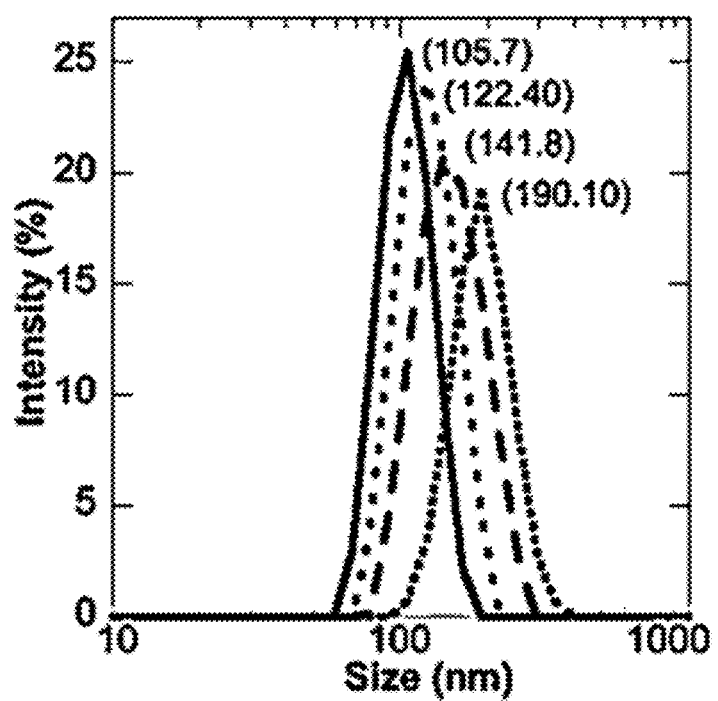
FIG. 14 shows DLS measurements of liposome (solid line) and CaPELs at various reaction quenching times of 0.25 hours (spaced dotted line), 3 hours (dashed line) and 20 hours (dotted line). The numbers in parentheses indicate the peak size values.
Figure 15:
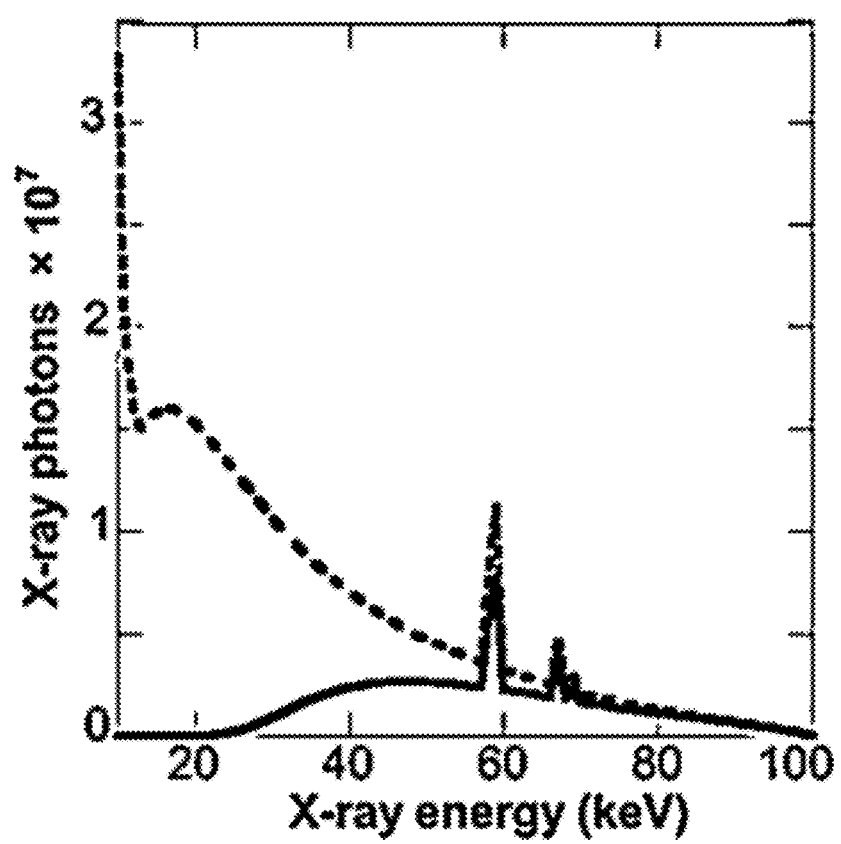
FIG. 15 shows X-ray spectra of unfiltered (dashed line) and filtered through a 0.125-mm Cu foil (solid line). Average X-ray energy shifts to 51.7 keV after filtration compared to an average X-ray energy of 32.7 keV in the unfiltered case.

Other experiments were performed to further explore the origin of the enhancement jump at 0.2/0.25 wp. Five different nanomaterials were prepared and the results were compared with the theoretical simulation results. Because T2PE needs short distances between AuNPs and CaPELs, the first modification was to vary the thickness of CaP in CaPELs. By varying the incubation time, 8-nm and 50-nm thick CaP coated CaPELs were also obtained. For 8-nm CaP shells, the enhancement jump was 3.0 at 0.25 wp, which was higher than the enhancement jump for 15-nm thick CaP shell CaPELs. The enhancement for the thicker 50-nm CaP layer (diamond) was only 0.25 fold for 1 wp Au and there was no jump. TEM inspection showed excessive CaP coating in 50-nm CaP samples (FIG. 13). DLS results are shown in FIG. 14, indicating a similar outcome. The second modification was adding PEG ligands into CaPEL solution before adding AuNPs. The enhancement measurements showed no jump. The third modification was to use different sizes of AuNPs because T2PE depends on the size of AuNPs. The results using 45 and 240 nm AuNPs are shown in FIG. 7A, which shows a smoother jump for 45 nm AuNPs (circle) and no jump for 240 nm (diamond) AuNPs. The fourth modification was to change from AuNPs to silica-covered gold nanoparticles (AuNPs@$SiO_2$). There was also no jump and slope of the enhancement was 0.75 $wp^{-1}$ for AuNPs@$SiO_2$. The results are shown in FIG. 7B (circle). Based on earlier studies, the enhancement also depends on X-ray spectrum. For example, T1PE is only 0.2-0.3 $wp^{-1}$ for AuNP@$SiO_2$ when unfiltered X-rays were used, due to the attenuation of low energy electrons by $SiO_2$ layer. After X-ray spectrum was filtered to remove low energy X-rays T1PE became 1.0 $wp^{-1}$. Hence the last modification was to change X-ray energy spectrum. The results are shown in FIG. 7B (diamond), which reveals that T2PE using filtered spectrum is the same as unfiltered X-ray spectrum. The X-ray spectra are shown in FIG. 15.

The enhancement results shown in FIGS. 6 and 7 can be understood with the assistance of theoretical simulation. As stated earlier, the maximum T2PE could be as high as 40 fold for a 800 diameter AuNP and this enhancement is defined as the increased energy deposition within the 5-nm thick layer at the surface of an 800-nm diameter AuNP for a single AuNP according to theoretical studies. The term "at" again means the 5-nm shell is in contact with the surface. For a CaPEL near a 90-nm diameter AuNP, the enhanced energy deposition enhancement was lower because it was averaged over the whole liposome inner volume (68-nm diameter was chosen) rather than the first 5-nm layer next to the AuNP surface. Therefore, this enhancement can better be described by a process of energy transfer from the AuNP to the CaPEL rather than T2PE in an arbitrarily defined space such as the 5-nm around the spherical nanoparticle. As stated earlier, this energy transfer is the aforementioned X-ray induced energy transfer or XIET, which more accurately and conveniently depicts the enhancement process.

Figure 8A:
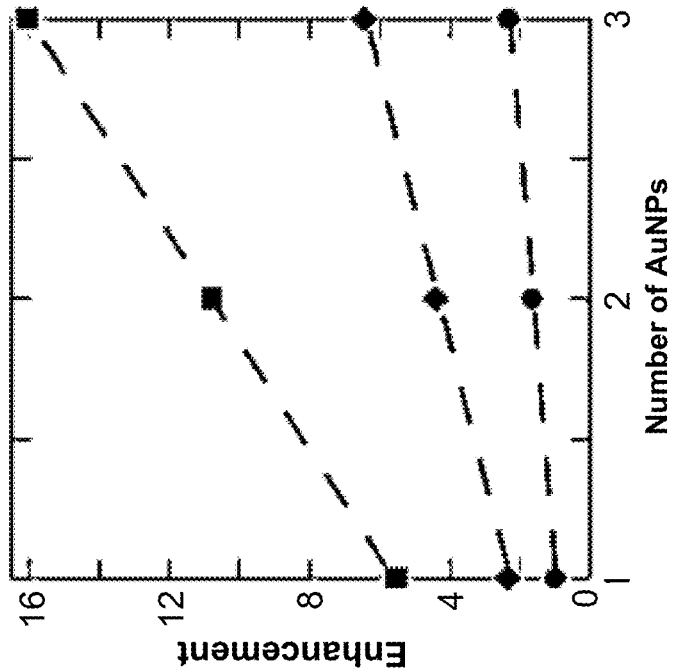
FIGS. 8A and 8B illustrate the relationships between various parameters and enhancement.
Figure 8B:
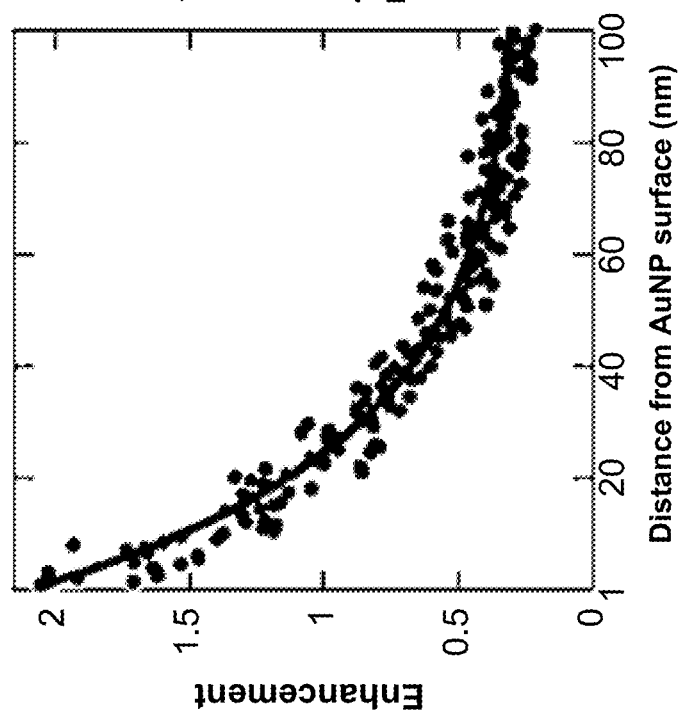
Figure 9:
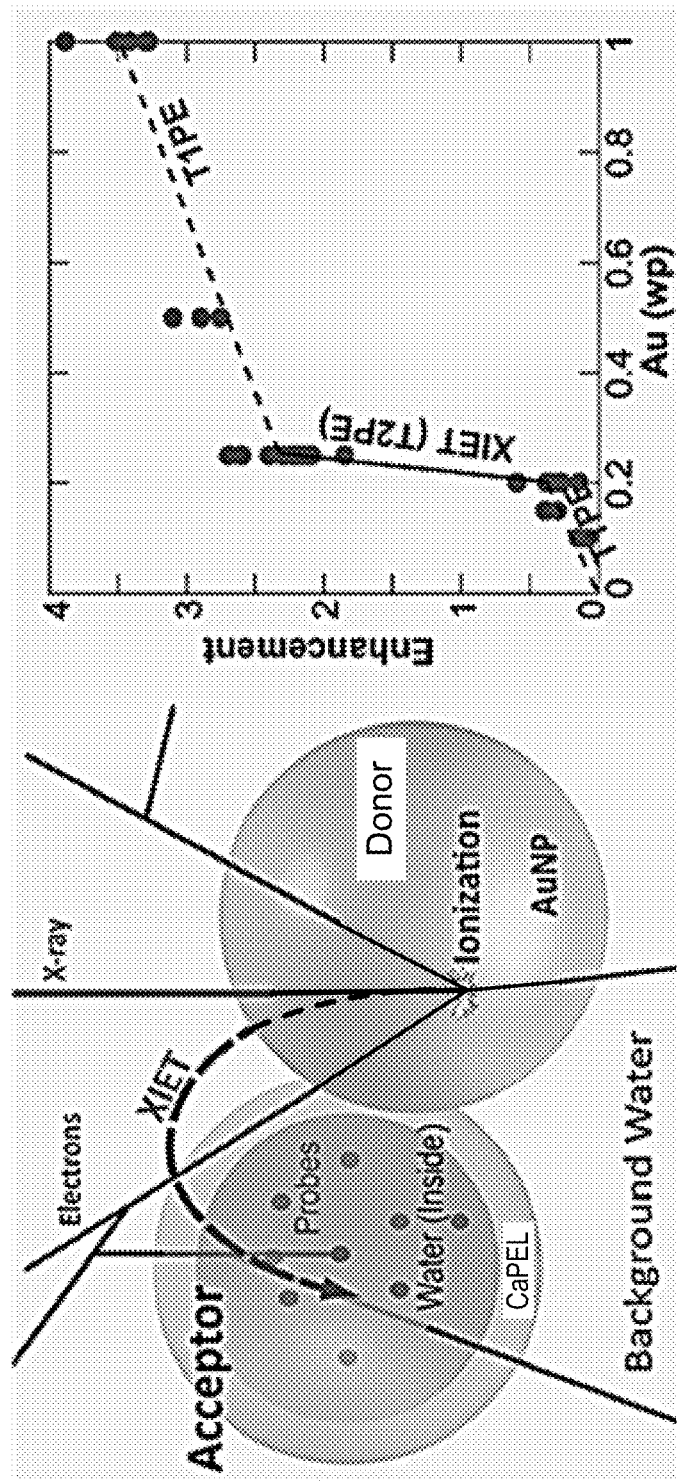
FIG. 9 shows a schematic depicting XIET between an AuNP donor and CaPEL acceptor and a graph of the relationship between gold weight percentage and enhancement.

The results of theoretical simulation of XIET from one AuNP to one CaPEL are shown in FIG. 8. FIG. 8A shows the distance dependency of XIET for a 90-nm AuNP next to a CaPEL. The XIET-based enhancement is 2.05 fold when the two are in contact and is 0.15 fold when they are 100 nm apart. The fluctuation in the predicted enhancement was caused by the limited number of trajectories used in the simulation. The enhancement shown here was scaled according to water, so if the enhancement was equal to that from water, then an absolute enhancement of 1.0 was obtained (relative enhancement=2.0). The enhancement followed an exponential decay curve with a decay constant of 32 nm. The enhancement was integrated over the CaPEL inner volume with a 0.5 nm step radially from the AuNP surface (round spots) and the results were fitted to obtain an average (solid line). The decay constant depends on the size of AuNPs and the size of CaPELs. The size effect of AuNPs on the enhancement was simulated and the results are shown in FIG. 8B, which shows the simulated enhancement for one, two and three AuNPs of different diameters (red round—45 nm, blue diamond—90 nm, and green square—240 nm respectively) in contact with a CaPEL. The 240 nm AuNPs provided a 6-fold enhancement whereas 45 nm AuNPs only 1.0 fold. FIG. 8B also shows simulation results for different numbers of AuNPs around a CaPEL. The enhancement increased linearly as the number of AuNPs increased.

These enhancement simulation results suggest that the experimentally observed jump can be explained by a single 90-nm AuNP in contact with a CaPEL and if 100% CaPELs are in such position at greater than 0.46 nM. Below this concentration, the percentage should be close to zero and there is no T2PE, and only T1PE exists. The results also suggest that it is unlikely to have multiple AuNPs at varying distances surrounding a CaPEL because otherwise the enhancement would not have the distinct jump; it would continuously and smoothly increase as the concentration of AuNPs increases. Therefore, the most probable and also the simplest explanation for the jump is caused by T2PE and there is only one AuNP is in contact with a CaPEL at above 0.2/0.25 wp Au or 0.46 nM AuNPs. The gentle slope of 1.0 $wp^{-1}$ slope is caused by T1PE, which agrees with published report and demonstrates the validity of using CaPELs as the probe for enhancement. In the framework of XIET, it is possible to express the enhancement as XIET(AuNP→CaPEL, T2PE=2.0 $NP^{-1}$) and XIET(AuNPs, T1PE=1.0 wp-1) as the outcome of this work. The results demonstrate that T2PE is caused by individual nanoparticles and T1PE by the entire sample. T2PE is therefore location dependent whereas T1PE is over the entire volume, including the region where T2PE exists. As shown in FIG. 8A, XIET follows an exponential decay curve as a function of the distance between the donors and acceptors. This work therefore demonstrates the existence and magnitude of T2PE in the framework of XIET.

After assigning the jump to T2PE and the gentle slope to T1PE, it is evident that the results shown in FIG. 6 indicate the total enhancement is the addition of T1PE and T2PE, i.e., T1PE and T2PE obey the addition algorithm, which is different from T1PE and CE that follow the multiplication algorithm.

Discussion

The experimental results shown in FIG. 7 can be explained by the proposed theoretical model of enhancement jump being caused by the AuNPs in contact with CaPELs. For example, adding PEG to CaPEL solution prior to adding PEGylated AuNPs reduced the attraction between PEGylated AuNPs and CaPELs, therefore stopping AuNPs-CaPELs association and eliminating T2PE. The results of the simulated enhancement for AuNP@$SiO_2$ suggest a 1.5-fold enhancement, which was different from the experimental observation. Without being bound to any particular theory, this was probably caused by the repulsion between AuNP@$SiO_2$ and CaPELs because both surfaces are negatively charged, based on zeta potential measurements reported in the literature. The shell thickness experimental results also agreed with the theoretical simulations, with 8-nm thick CaP producing higher enhancement and 50-nm thick CaP producing little enhancement. For the size effect, the reason the jump was not observed experimentally for 240-nm AuNPs was most likely due to the concentration of these nanoparticles being too low—at the same wp, 240-nm AuNP was 10 fold more dilute than 90 nm AuNPs. For 45 nm AuNPs, the experimentally observed jump of about 1.0 fold matched the simulated value of 1.0. At higher AuNP concentrations, the experimentally measured enhancements were slightly higher that predicted enhancement from one 45-nm AuNP in contact with a CaPEL, suggesting that there may be more than one 45-nm AuNPs next to a CaPEL at high AuNP concentrations. This was anticipated because it has been shown that for small AuNPs, more than one AuNP are in contact with one nanoparticle.

XIET described here resembles the molecular energy transfer probe counterpart of Förster resonance energy transfer (FRET). The AuNP donors absorb X-rays and emit electrons that deposit energy in CaPELs acceptors. The differences between the two are that in XIET (1) ionizing radiation X-rays instead of visible photons are used to initiate energy transfer, (2) transfer is mediated by an electron or electrons rather than virtual fluorescent photons emitted from the donor depositing energy in the acceptor, and (3) the probe in the acceptors may be permanently altered and the enhancement can be measured ex situ. Because of the second difference, the distance dependency for XIET is exponential, as shown in this work. The spatial resolution depends on the size of the acceptor. The acceptor size may be smaller than the ~100 nm used here, and reduction in the acceptor size enables higher spatial resolution measurements. For example, proteins may be modified to use as the acceptor to study how nanomaterials interact with each other at high concentrations. Modified micelles or dendrimer nanoparticles are other candidates. Because X-rays are highly penetrating, XIET can be applied to studying highly concentrated, optically or electron microscopically opaque samples.

The observed results can be explained theoretically through the processes of T2PE and T1PE, with T1PE accounting for the slope of 1 $wp^{-1}$ and T2PE for the jump of 2 fold for 90-nm AuNPs with one AuNPs in contact with a CaPEL. If AuNPs were not within a close distance from CaPELs, then there was only T1PE. These outcomes were obtained without considering AE, which may affect the free SRB in CaPEL samples. For example, AE contribution at 0.2 wp was around 1%, therefore AE at this concentration did not affect the results. The calculated T2PE should be higher by 7% at 1.0 wp AuNP concentration, and the calculated the total enhancement in absence of AE would be 4.4 fold. This means that for unfiltered X-rays and if T1PE at this gold concentration is 1 $wp^{-1}$, then T2PE is 3.0 to 3.4 fold. These estimations show that for high concentrations of AuNPs and if there is a significant amount of free SRB in CaPEL solution, then AE may affect the enhancement measurement.

Conclusion

It was experimentally demonstrated for the first time a nanoscale probe that stores and shields probing molecules from the outside chemical environment can be used to probe T2PE. Because electrons can penetrate the calcium phosphate shell and reach the interior of calcium phosphate coated liposomes, the radicals generated therein can damage SRB probe molecules. As a result, physical enhancement was measured in the presence of large quantities of X-ray absorbers such as gold nanoparticles without interference from other factors such as chemical enhancement or anti-enhancement. The observed enhancement caused by T2PE was 2.0 fold for all CaPELs and this enhancement was equivalent to 42 fold wp$^{-1}$. T1PE is 1.0 fold wp$^{-1}$. The results shown here demonstrated that T2PE can be determined in the framework of XIET between AuNP donors and CaPEL acceptors and the results reveal that T1PE and T2PE obey the addition algorithm.

Supplementary Information

Additional information regarding experimental and theoretical procedures sample preparation, irradiation protocols, enhancement calculations, enhancement simulation, and theoretical modeling are described below.

A. Experimental Methods

A1. Materials 30 weight percent (wp) gold (III) chloride solution (99.99% trace metals basis) in dilute HCl, sodium citrate tribasic dihydrate (ACS reagent≥99%), phosphoric acid (crystalline, ≥99.999% trace metals basis) and 2-carboxyethanephosphonic acid (94%, CEPA) were purchased from Sigma Aldrich. Calcium chloride (anhydrous, extra pure, 96%), sodium hydroxide (pellets, certified ACS, ≥97%), sulforhodamine B (97%, SRB), chloroform (99.8%), and ferrous sulfate (certified ACS) were purchased from Fisher Scientific. 1,2-dioleoyl-sn-glycero-3-phosphate (sodium salt, DOPA) lipid was purchased from Avanti Polar Lipids Inc. Hydrogen peroxide (30% certified ACS) solution was purchased from Meron Fine Chemicals. Methoxy polyethylene glycol thiol (mPEG-SH, $M_w$ 5000) was purchased from Laysan Bio as well as Nanocs Inc. Silane methoxy polyethylene glycol thiol (Silane mPEG-SH, $M_w$ 5000) was purchased from Laysan Bio. MilliQ water (MQ, 18.3 MΩ) was used throughout the experiments. SpecVette™ cuvettes were purchased from ALine Inc.

A2. Syntheses

Synthesis of 45, 90 and 240 nm AuNPs 90 nm gold nanoparticles (AuNPs) were synthesized using a modified Frens protocol (33). Briefly, 61 μL gold (III) chloride solution was added to 300 mL MQ $H_2O$, which was boiled under reflux condition and vigorous stirring (approximately 1100 RPM). 1.2 mL of 1% sodium citrate was quickly added to the solution under vigorous stirring. Stirring speed was reduced to approximately 500 RPM for the next 25 min. 30 mg of mPEG-SH dissolved in 1 mL of $H_2O$ with 15 min. sonication were used for PEGylation of AuNPs. The sonicated mPEG-SH solution was added to the cooled AuNP solution at room temperature and the reaction was allowed to proceed overnight. The AuNPs were concentrated using repeated centrifugation and the amount of gold was determined using an atomic absorption spectrometer (Varian 220FS). Different size AuNPs were synthesized by changing the amount of sodium citrate used in the synthesis. 45 nm AuNPs were obtained by using 3.5 mL of 1% sodium citrate and 240 nm AuNPs were obtained by using 0.4 mL of 1% sodium citrate with other constituents remaining the same. Both 45 and 240 nm AuNPs were PEGylated using 1 mL sonicated solutions of 60 mg and 15 mg of mPEG-SH, respectively. PEGylated AuNPs are noted as AuNPs here unless stated otherwise.

Synthesis of SRB-Containing CaPELs

The CaPELs were synthesized using a modified procedure given by Schimdt (34). 25 mg DOPA lipid was dissolved in 5 mL chloroform to prepare a 5 mg/mL solution. 0.5 mL of the DOPA solution was put in a 25 mL round bottom flask and air-dried to remove chloroform under argon to form a thin film of lipid. The dried film was further dried under vacuum for 4 hours in a rotary evaporator to remove trace amounts of chloroform. The lipid was then hydrated for 1 hour under constant rotation using 0.5 mL of 1 mM SRB aqueous solution. After nine freeze-thaw cycles the lipid were extruded through a mini extruder 21 times. The extruded liposomes were stored for 1 hour before calcium phosphate coating. Calcium phosphate coating of the liposomes was achieved as follows: 10 μL of 1 M phosphoric acid and 40 μL of 1 M sodium hydroxide solution were added to 50 mL of $H_2O$. pH of the resulting solution was 10.3. 150 μL of SRB-in-liposome solution was added into the solution and the mixture was stirred at 400 RPM, followed quickly (within 5 sec.) by the addition of 100 μL of 0.1 M $CaCl_2$) solution. The solution was allowed to react under stirring and the reaction was quenched using 50 μL of 0.1 M CEPA solution at quenching time of 0.25, 3, 10 or 20 hours to achieve different thicknesses of calcium phosphate coating. The samples were allowed to incubate for another 30 hours prior to purification by dialysis. FIG. 13 shows TEM images of CaPELs obtained using three incubation times.

Synthesis of CaPELs without SRB

The CaPELs without SRB were prepared in the same way as the SRB encapsulating CaPELs described above. The only difference was the use of 0.5 mL of MQ water in lieu of SRB aqueous solution. The samples were dialyzed to remove unreacted reactants.

Absorption Spectra of Highly Concentrated 90 nm AuNPs

The absorption spectra of highly concentrated AuNPs (up to 1 wp) was measured using a Shimadzu UV-VIS-NIR spectrophotometer (UV1700) in a 500 μm path length cuvette (SpecVette™ 500 μm).

Synthesis of Au@$SiO_2$

The silica coated AuNPs were synthesized using a modified protocol from (35) and was reported in a previously published article by this group (3).

Fenton Reactions

Figure 16:
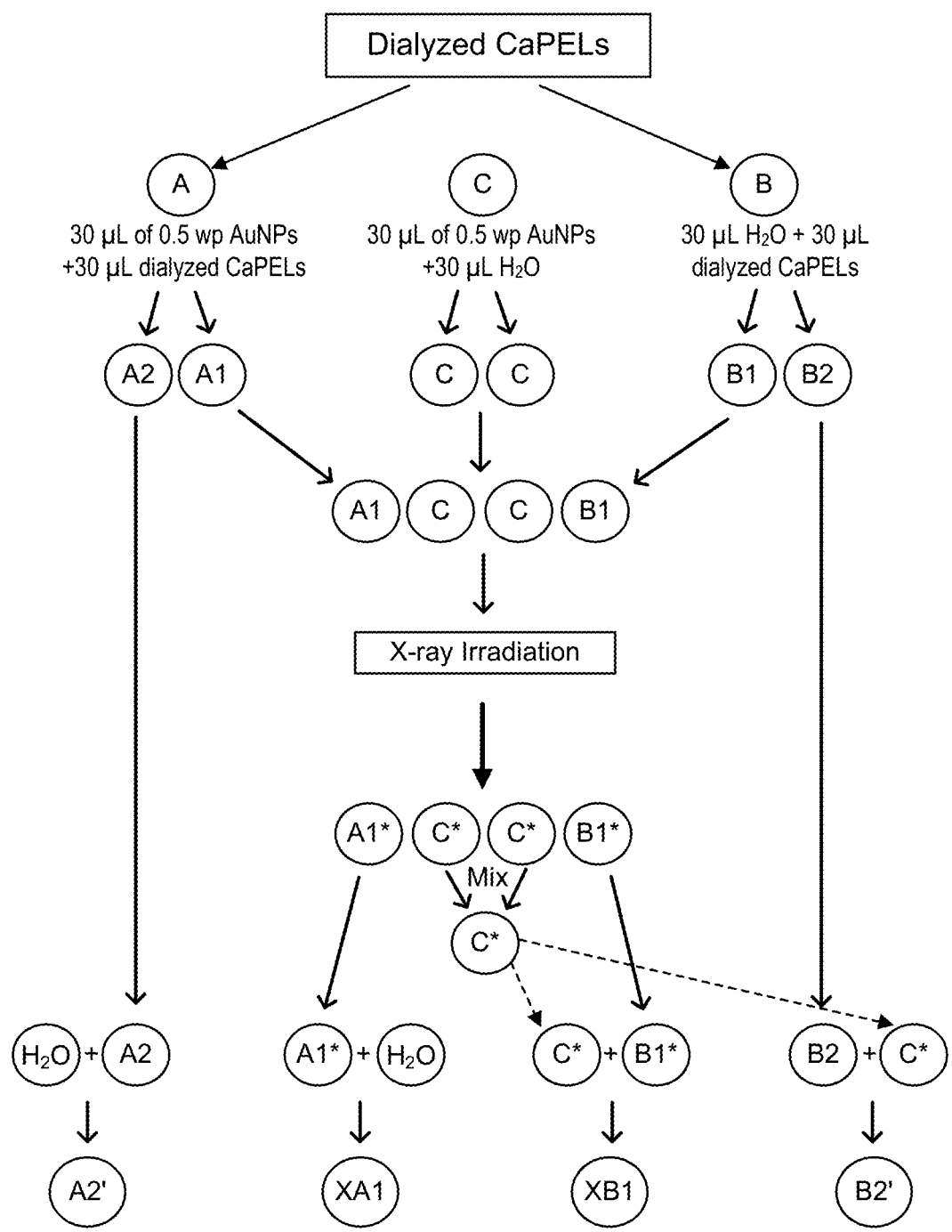
FIG. 16 depicts an irradiation scheme of CaPELs to determine enhancement. A2', XA1, XB1 and B2' were diluted to 75 µL by adding 15 µL Mili-Q water prior to centrifugation for 25 min. at 1500 RPM to remove AuNPs. The supernatants were used for fluorescence measurements.

The 1 mL dialyzed CaPELs were treated with 1 mL 0.1 mM Fe (II) and 1 mL of 2 mM $H_2O_2$ in order to remove the free SRB. 30 μL of the Fenton treated samples were used for X-ray irradiation with different concentrations of 90 nm AuNPs. The samples for irradiation were prepared according to FIG. 16. The only difference was the use of Fenton treated CaPELs in place of dialyzed CaPELs.

Diluted Experiments

The 1 mL dialyzed CaPELs were diluted to 10 mL using MQ water. 30 μL of the 10× diluted samples were used for X-ray irradiation with different concentrations of 90 nm AuNPs.

Filtered X-Ray Experiments

X-rays were filtered through a 0.125-mm Cu foil. The filtered X-rays have an average energy of approximately 51.7 keV. FIG. 15 shows the spectra of unfiltered and filtered X-rays.

Nanoparticle Characterization

The nanoparticles were characterized using TEM and dynamic light scattering (DLS) measurements. FIG. 14 shows the DLS results of liposomes and CaPELs. For TEM 8 μL of the dialyzed samples were drop dried onto a lacey carbon type-A 300 mesh copper grid and imaged under either Philips CM-12 or JEOL 1230 microscopes at 120 or 100 kV, respectively. Cryo-TEM was done on JEOL 2100F microscope. The DLS measurements were made using Malvern Zetasizer (Nano S90 fitted with a 633 nm laser). Fluorescence measurements were made using Yvon Horiba FluoroMax-4. Absorption measurements were made using either Shimadzu UV-VIS-NIR spectrophotometers (UV1700 and UV-3600).

A3. Experimental Procedures

The dialyzed CaPELs were mixed with AuNP solution prior to irradiation. The mixtures were purified using centrifugation to remove AuNPs prior to fluorescence measurements. The procedure for concentration of AuNPs was similar to the preparation of 0.25 wp AuNPs-CaPEL sample as described below.

30 µL of 0.5 wp AuNPs and 30 µL of dialyzed 0.2 kGy pre-irradiated CaPELs were mixed in a 500 µL Eppendorf tube (A). This solution was divided into two portions of 30 µL each (A1 and A2). One of the portions (A1) was irradiated with 1 kGy of X-rays whereas A2 was not. A control sample without AuNPs was prepared by mixing 30 µL of MQ water and 30 µL of dialyzed CaPEL in a 500 µL Eppendorf tube (B). This control was also divided into two portions of 30 µL each (B1 and B2) and solution B1 was irradiated with 1 kGy of X-rays, whereas solution B2 served as the non-irradiated control. The controls without gold (B1 and B2) were spiked with 30 µL irradiated AuNPs (C*). These experiments resulted in four samples of 60 µL in volume: XA1, A2', XB1 and B2'. Each sample was then diluted to 75 µL by adding 15 µL of MiliQ water. AuNPs were removed from these samples by centrifugation at 1500 RPM for 25 min. and their fluorescence was measured. The sample preparation is pictorially depicted in FIG. 16. The fluorescence signals with and without AuNPs and with and without X-ray irradiation were used to determine the SRB degradation rates, which were then used for enhancement calculation using a procedure shown in Section B below. All irradiations were performed using Kevex™ PXS10 130 kV MicroFocus X-ray source operated at 100 kV and 450 µA and fitted with a Cole-Parmer Remote-Monitoring Thermocouple Thermometer. Centrifugation was done on Fisher Scientific accuSpin™ 400 centrifuge.

A4. Anti-Enhancement (AE) Measurement

Although adding gold to a sample can cause increased absorption and possibly more energy deposited in the sample, adding AuNPs does not necessarily always cause increased yield of a dosimetric reaction due to the scavenging nature of AuNPs. FIG. 10 shows the measured signals (lower triangles) of adding 90 nm AuNPs to 0.3 µM SRB. Also shown is the signal without AuNPs (upper triangles). It is clear that there was an anti-enhancement (AE) of about 40% per 1 wp of 90-nm AuNPs. Because of AE, even after 1 kGy or 1.2 kGy of X-ray irradiation, there were minute and yet measurable amounts of free SRB. It was estimated that if there were 91% free and 9% trapped SRB in the original samples after dialysis, after 200 Gy of pre-irradiation these SRB became 22.3% and 8.64%, respectively. These signals and the corresponding SRB amounts were normalized to the original total fluorescence signal after dialysis, which was 100%. Because this irradiation was done without adding AuNPs, these amounts of SRB were the same for all experiments. With 0.2 wp AuNPs and after taking 0.4 wp$^{-1}$ AE into consideration, the amounts of unreacted SRB were 0.037% (outside) and 4.71% (inside) respectively after another 1.0 kGy irradiation. At 1 wp, the signals were 0.35% and 4.71%, respectively (i.e., no change to the signal from SRB inside CaPELs because AE did not affect it). The error introduced by not considering AE to the outside and free SRB was about 7% at 1 wp 90-nm AuNPs. It is thus reasonable to ignore AE in the enhancement calculation with less than 1 wp 90-nm AuNPs. However, at higher AuNP concentrations it is necessary to take AE into consideration.

B. Calculation of Experimental Enhancement

Figure 11A:
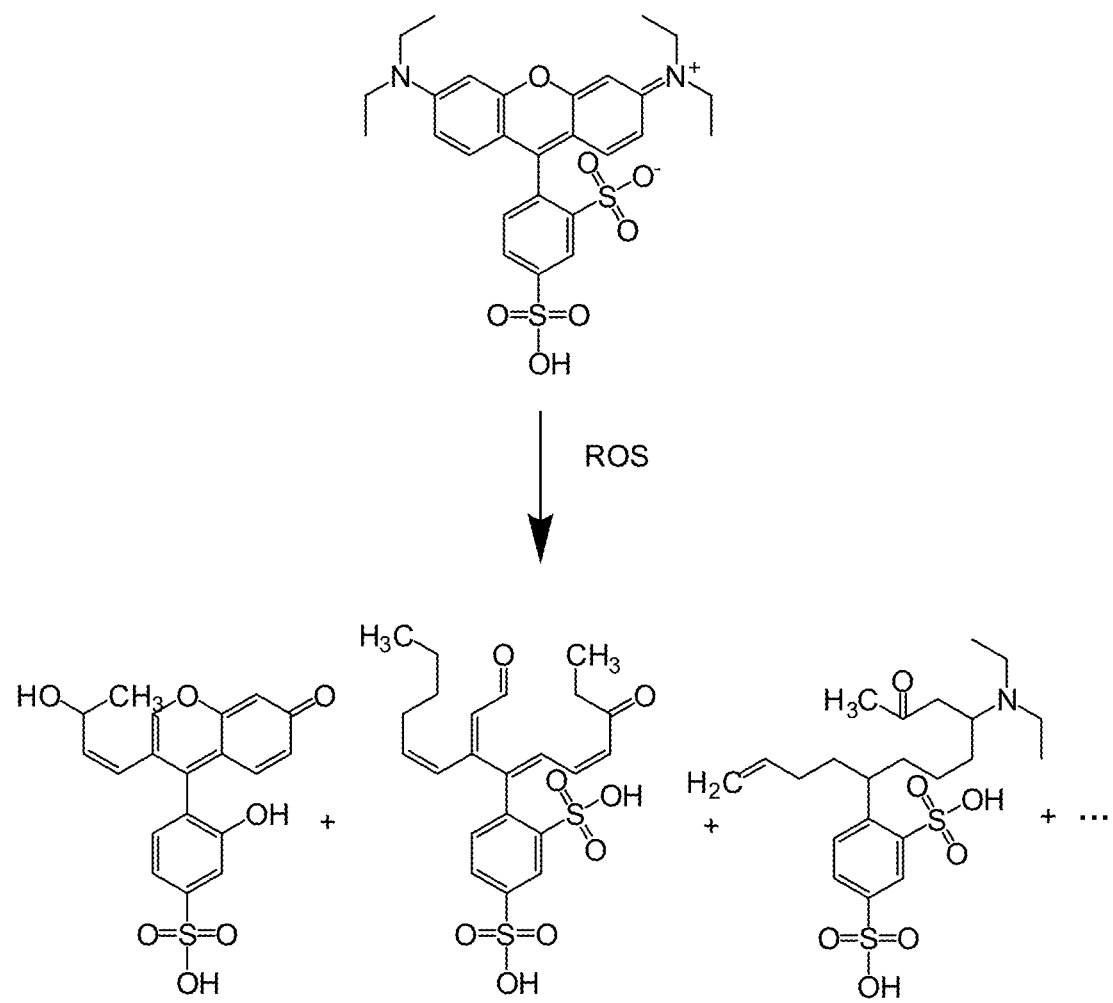
Figure 11B:
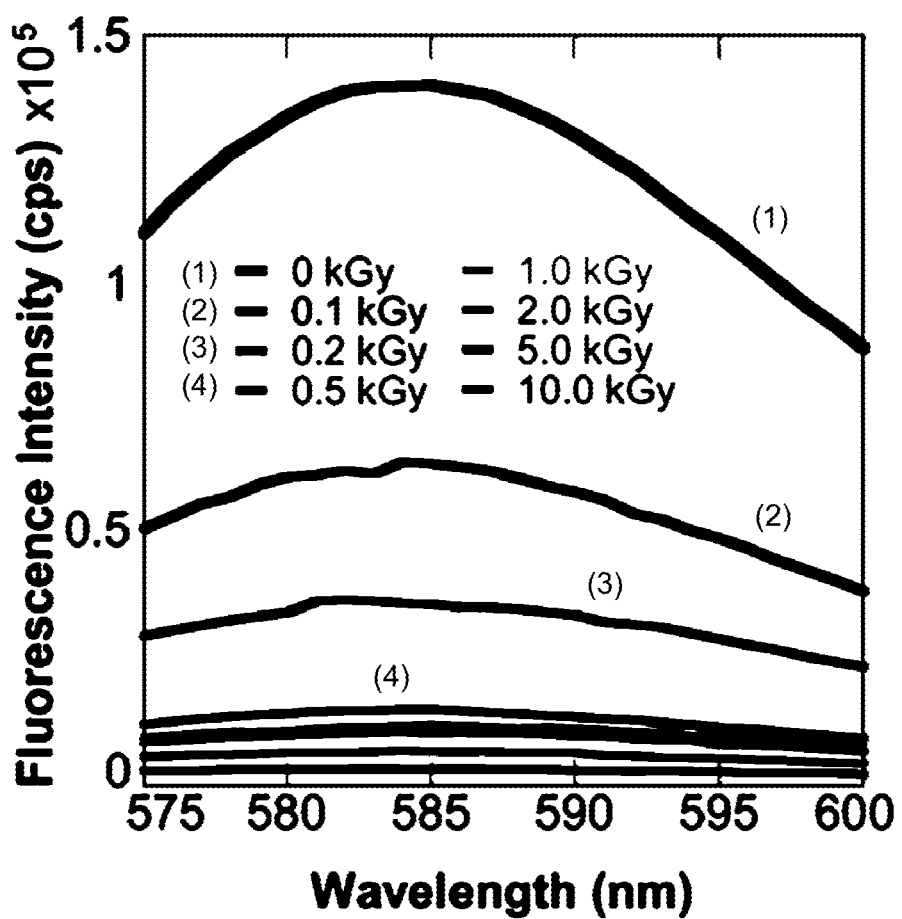

Enhancement was determined from the ratio of the amount of sulforhodamine B (SRB) dye degraded with to the amount degraded without gold nanoparticles under X-ray irradiation. Degradation of SRB is shown in FIG. 11A and fluorescence decay as a function of X-ray dose is shown in FIG. 11B.

The first step was to determine the baseline degradation of SRB inside CaPELs without AuNPs. Degradation of SRB dye inside of the as-prepared post-dialyzed CaPELs was measured after irradiation with 0-10 kGy of X-ray radiation and fitted with double exponential decays as shown in FIGS. 8A and 8B in the main text and FIGS. 11C and 11D. The fluorescent SRB molecules were decomposed by ROS such as hydroxyl radicals into several non-fluorescent products (22).

The degradation of SRB followed the form of exponential decay with two rates: fast and slow. The fast component was due to free SRB in solution (the free SRB in solution that could not be dialyzed even after 24 hours of dialysis). The slower rate was the SRB degradation inside the CaPELs. The fitting showed the following rates of dose dependency of the degradation of SRB outside and inside the CaPELs (FIG. 11C):

$$I_x = I_0^{(free)} e^{-9.1x} + I_0^{(trapped)} e^{-0.15x} \quad \text{(Eq. 1)}$$

where 9.1 kGy$^{-1}$ and 0.15 kGy$^{-1}$ are the degradation rate constants (k) used to fit the experimental data and x is the dose of X-ray radiation in kGy.

Figure 11D:
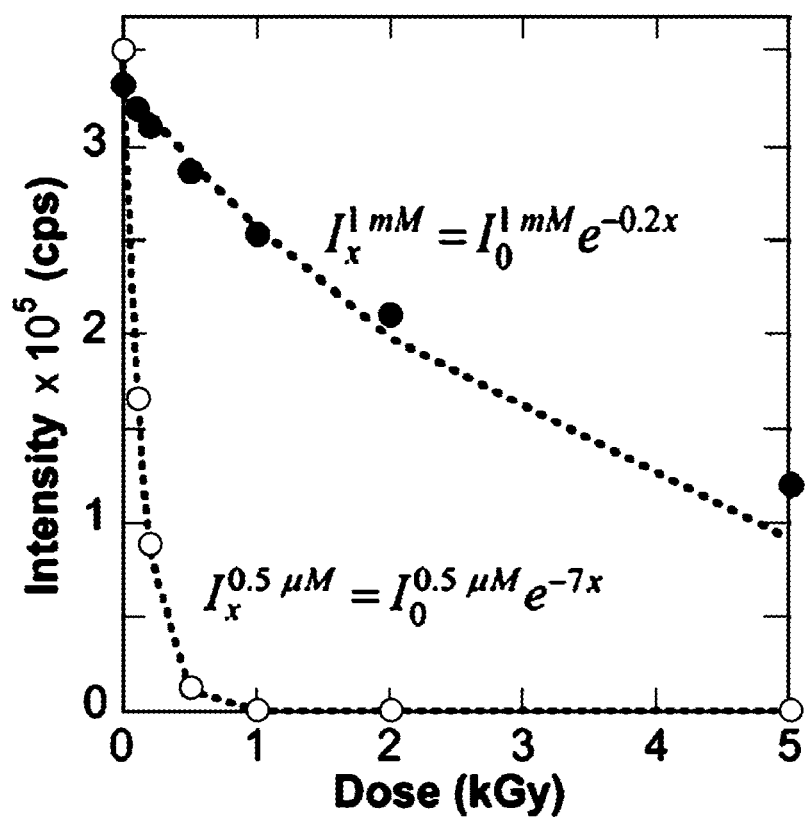

These dependencies were supported by the degradation rate of 0.5 µM SRB and 1 mM SRB aqueous solutions, as shown in FIG. 11D. Because CaPELs were prepared by incubating with 1 mM SRB solution, it was expected that SRB inside the CAPELs were also at approximately 1 mM. The initial degradation (up to 2 kGy) of free 1 mM SRB solution was:

$$I_x^{1\ mM} = I_0^{1\ mM} e^{-0.2x} \quad \text{(Eq. 2)}$$

whereas, for 0.5 µM SRB solution the decay was:

$$I_x^{0.5\ \mu M} = I_0^{0.5\ \mu M} e^{-7x} \quad \text{(Eq. 3)}$$

It was therefore concluded that the concentration of encapsulated or trapped SRB was close to 1 mM and the concentration of free SRB in CaPEL samples were slightly less than 0.5 µM. Eq. 1 can be used to calculate the amount of free and encapsulated SRB that are still intact and the ratio of the amounts with and without AuNPs gives rise to the enhancement and therefore the efficiency of XIET. The enhancement is defined as the ratio of the increased degradation rate of SRB inside CaPELs in presence of AuNPs to without AuNPs after both are irradiated with 1 kGy of X-rays.

$$\text{Enhancement} = \frac{SRB\ (\text{inside } CaPEL)\ \text{degredation rate with } AuNP}{SRB\ (\text{inside } CaPEL)\ \text{degredation rate without } AuNF} - 1.0 \quad (4)$$

This enhancement is the absolute enhancement, meaning there is no enhancement (enhancement=0) when there are no AuNPs. It should be noted that the CaPELs samples were pre-irradiated with 0.2 Gy of X-rays prior to irradiation with 1 kGy of radiation in order to minimize the amount of free SRB in the samples.

Example of Enhancement Calculation for 0.25 wp Au

An example of enhancement calculation at 0.25 wp of AuNPs is shown below. The abbreviations indicating the samples are detailed in FIG. 16.

Step 1

An SRB degradation profile for trapped SRB inside CaPELs in the presence of a low concentration of free SRB in the sample solution is shown in FIG. 11C. The mathematical fit is:

$$I_x = I_0^{(free)} e^{-9.1x} + I_0^{(trapped)} e^{-0.15x}$$

where, x=X-ray dose in kGy.

Step 2

Enhancement calculation: The fluorescence (in cps) from the measured samples were as follows:

A2'=39201, XA1=10891, B2'=41296, XB1=15801.

FIG. 11D shows that for a SRB solution of which the concentration is similar to the free SRB concentration in CaPEL solution the fluorescence from free SRB after 1 kGy is negligible, so it can be assumed that after a total of 1.2 kGy the contribution from free SRB can be disregarded. Therefore in XA1 and XB1 the fluorescence is considered to be due to the trapped SRB only. Therefore the amount of trapped SRB in 0.2 kGy pre-irradiated sample (B) can be calculated as:

$$I_{XB1}^{(trapped)} = I_{B2'}^{(trapped)} e^{-0.15 \times 1} \Rightarrow I_{B2'}^{(trapped)} = \frac{I_{XB1}^{(trapped)}}{e^{-0.15 \times 1}} = 18358$$

The amount of trapped SRB in sample A2' is same as that in sample B2' as they are part of the same initial CaPEL sample.

The rate of trapped SRB damage in the sample without AuNPs (ie. B2'→XB1) is obtained from the fit, k (No Au)=0.15 kGy$^{-1}$.

The rate of trapped SRB damage in sample with AuNPs (i.e., A2'→XA1) can be calculated as:

$$I_{XA1}^{(trapped)} = I_{A2'}^{(trapped)} e^{-k(Au) \times 1} =$$

$$I_{B2'}^{(trapped)} e^{-k(Au) \times 1} \Rightarrow k(Au) = -\ln\left(\frac{I_{XA1}^{(trapped)}}{I_{B2'}^{(trapped)}}\right) = 0.478 \ kGy^{-1}$$

Therefore, $$\text{Enhancement} = \left(\frac{k(Au)}{k(\text{No } Au)}\right) - 1.0 = \left(\frac{0.478}{0.15}\right) - 1.0 = 2.19$$

C. Theoretical Enhancement Simulation

A modified Monte-Carlo-based method implemented in Mathematica and C++ was used to simulate the energy deposition by gold nanoparticles under X-ray irradiation. Many details of the original methodology have been published previously by this group (13). Briefly, the code generated photoelectrons and Auger electrons for each absorbed X-ray photon according to the probability of electron energy distribution. The rate of photon absorption was determined by the absorption cross-section, density, volume of the material and the X-ray photon flux. The calculations were made in an aqueous solution and the contribution from water was assumed to be uniform over the whole volume. The enhancement was defined as the ratio of the energy deposition in the presence of added nanostructures in water to when the nanostructures are absent (i.e., pure water). The contribution from the background water was then subtracted (i.e., simulated enhancement minus 1.0). FIG. 12 shows simulated enhancements of a CaPEL having an inner spherical cavity with a diameter of 64 nm with one, two or three gold nanoparticles attached to the CaPEL. One set of data (diamonds) was obtained with 30 keV monochromatic X-rays and another set (circles) averaged over an X-ray spectrum covering 10-100 keV. The difference between the two simulated enhancements was less than 5%. As a result, the monochromatic X-ray was used in the enhancement simulation.

REFERENCES (1) Starkewolf, Z. B.; Miyachi, L.; Wong, J.; Guo, T. X-Ray Triggered Release of Doxorubicin from Nanoparticle Drug Carriers for Cancer Therapy. Chem. Commun. 2013, 49, 2545-2547.

(2) Davidson, R. A.; Guo, T. An Example of X-Ray Nanochemistry: Sers Investigation of Polymerization Enhanced by Nanostructures under X-Ray Irradiation. J Phys Chem Lett 2012, 3, 3271-3275.

(3) Cheng, N. N.; Starkewolf, Z.; Davidson, A. R.; Sharmah, A.; Lee, C.; Lien, J.; Guo, T. Chemical Enhancement by Nanomaterials under X-Ray Irradiation. J. Am. Chem. Soc. Commun. 2012, 134, 1950-1953 1950.

(4) Guo, T. Nanoparticle Enhanced X-Ray Therapy. In ACS Annual Meeting Philadelphia, Pa., August, 2004.

(5) Hainfeld, J.; Slatkin, D.; Smilowitz, H. The Use of Gold Nanoparticles to Enhance Radiotherapy in Mice. Phys. Med. Bio. 2004, 49, N309-N315.

(6) Foley, E.; Carter, J.; Shan, F.; Guo, T. Enhanced Relaxation of Nanoparticle-Bound Supercoiled DNA in X-Ray Radiation. Chem. Commun. 2005, 3192-3194.

(7) Cho, S. H. Estimation of Tumor Dose Enhancement Due to Gold Nanoparticles During Typical Radiation Treatments: A Preliminary Monte Carlo Study. Med. Phys. 2005, 32, 2162-2162.

(8) Zheng, Y.; Hunting, D. J.; Ayotte, P.; Sanche, L. Radiosensitization of DNA by Gold Nanoparticles Irradiated with High-Energy Electrons. Radiat. Res. 2008, 169, 19-27.

(9) McMahon, S. J.; Hyland, W. B.; Brun, E.; Butterworth, K. T.; Coulter, J. A.; Douki, T.; Hirst, D. G.; Jain, S.; Kavanagh, A. P.; Krpetic, Z. et al. Energy Dependence of Gold Nanoparticle Radiosensitization in Plasmid DNA. J. Phys. Chem. C 2011, 115, 20160-20167.

(10) Butterworth, K. T.; Wyer, J. A.; Brennan-Fournet, M.; Latimer, C. J.; Shah, M. B.; Currell, F. J.; Hirst, D. G. Variation of Strand Break Yield for Plasmid DNA Irradiated with High-Z Metal Nanoparticles. Radiat. Res. 2008, 170, 381-387.

(11) Sicard-Roselli, C.; Brun, E.; Duchambon, P.; Blouquit, Y.; Keller, G.; Sanche, L. Gold Nanoparticles Enhance the X-Ray-Induced Degradation of Human Centrin 2 Protein. Radiat. Phys. Chem. 2009, 78, 177-183.

(12) Guidelli, E. J.; Ramos, A. P.; Zaniquelli, M. E. D.; Nicolucci, P.; Baffa, O. Synthesis and Characterization of Silver/Alanine Nanocomposites for Radiation Detection in Medical Applications: The Influence of Particle Size on the Detection Properties. Nanoscale 2012, 4, 2884-2893.

(13) Lee, C.; Cheng, N. N.; Davidson, R. A.; Guo, T. Geometry Enhancement of Nanoscale Energy Deposition by X-Rays. J. Phys. Chem. C 2012, 116, 11292-11297.

(14) Davidson, R. A.; Guo, T. Average Physical Enhancement by Nanomaterials under X-Ray Irradiation. J. Phys. Chem. C 2014, 118, 30221-30228.
(15) Carter, J. D.; Cheng, N. N.; Qu, Y. Q.; Suarez, G. D.; Guo, T. Nanoscale Energy Deposition by X-Ray Absorbing Nanostructures. J. Phys. Chem. B 2007, 111, 11622-11625.
(16) Amato, E.; Italiano, A.; Leotta, S.; Pergolizzi, S.; Torrisi, L. Monte Carlo Study of the Dose Enhancement Effect of Gold Nanoparticles During X-Ray Therapies and Evaluation of the Anti-Angiogenic Effect on Tumour Capillary Vessels. J X-Ray Sci Technol 2013, 21, 237-247.
(17) Yang, W. S.; Read, P. W.; Mi, J.; Baisden, J. M.; Reardon, K. A.; Lamer, J. M.; Helmke, B. P.; Sheng, K. Semiconductor Nanoparticles as Energy Mediators for Photosensitizer-Enhanced Radiotherapy. Int. J. Radiat. Oncol. Biol. Phys. 2008, 72, 633-635.
(18) Chen, H. M.; Wang, G. D.; Chuang, Y. J.; Zhen, Z. P.; Chen, X. Y.; Biddinger, P.; Hao, Z. L.; Liu, F.; Shen, B. Z.; Pan, Z. W.; Xie, J. Nanoscintillator-Mediated X-Ray Inducible Photodynamic Therapy for in Vivo Cancer Treatment. Nano Lett. 2015, 15, 2249-2256.
(19) Anzai, K.; Aikawa, T.; Furukawa, Y.; Matsushima, Y.; Urano, S.; Ozawa, T. Esr Measurement of Rapid Penetration of Dmpo and Depmpo Spin Traps through Lipid Bilayer Membranes. Arch. Biochem. Biophys. 2003, 415, 251-256.
(20) Fortier, C. A.; Guan, B.; Cole, R. B.; Tarr, M. A. Covalently Bound Fluorescent Probes as Reporters for Hydroxyl Radical Penetration into Liposomal Membranes. Free Radic. Biol. Med. 2009, 46, 1376-1385.
(21) Chanana, M.; Liz-Marzan, L. M. Coating Matters: The Influence of Coating Materials on the Optical Properties of Gold Nanoparticles. Nanophotonics-Berlin 2012, 1, 199-220.
(22) Gosetti, F.; Bolfi, B.; Marengo, E. Identification of Sulforhodamine B Photodegradation Products Present in Nonpermanent Tattoos by Micro Liquid Chromatography Coupled with Tandem High-Resolution Mass Spectrometry. Anal. Bioanal. Chem. 2015, 407, 4649-4659.
(23) Zhao, W.; Chen, C. C.; Li, X. Z.; Zhao, J. C.; Hidaka, H.; Serpone, N. Photodegradation of Sulforhodamine-B Dye in Platinized Titania Dispersions under Visible Light Irradiation: Influence of Platinum as a Functional Co-Catalyst. J. Phys. Chem. B 2002, 106, 5022-5028.
(24) Cheng, M. M.; Ma, W. H.; Li, J.; Huang, Y. P.; Zhao, J. C. Visible-Light-Assisted Degradation of Dye Pollutants over Fe(Iii)-Loaded Resin in the Presence of H2o2 at Neutral Ph Values. Environ. Sci. Technol. 2004, 38, 1569-1575.
(25) Okada, T. Efficient Evaluation of Poly(Oxyethylene) Complex-Formation with Alkali-Metal Cations. Macromolecules 1990, 23, 4216-4219.
(26) Davidson, R. A.; Guo, T. Multiplication Algorithm for Combined Physical and Chemical Enhancement of X-Ray Effect by Nanomaterials. J. Phys. Chem. C 2015, 119, 19513-19519.
(27) Yeo, C. H.; Zein, S. H. S.; Ahmad, A. L.; McPhail, D. S. Comparison of Dopa and Dppa Liposome Templates for the Synthesis of Calcium Phosphate Nanoshells. Ceram. Int. 2012, 38, 561-570.
(28) Sadtler, B.; Wei, A. Spherical Ensembles of Gold Nanoparticles on Silica: Electrostatic and Size Effects. Chem. Commun. 2002, 1604-1605.
(29) McConnell, M. D.; Bassani, A. W.; Yang, S.; Composto, R. J. Tunable Wetting of Nanoparticle-Decorated Polymer Films. Langmuir 2009, 25, 11014-11020.
(30) Sahoo, H. Forster Resonance Energy Transfer—a Spectroscopic Nanoruler: Principle and Applications. J Photoch Photobio C 2011, 12, 20-30.
(31) Guo, R.; Wang, H.; Peng, C.; Shen, M. W.; Zheng, L. F.; Zhang, G. X.; Shi, X. Y. Enhanced X-Ray Attenuation Property of Dendrimer-Entrapped Gold Nanoparticles Complexed with Diatrizoic Acid. J. Mater. Chem. 2011, 21, 5120-5127.
(32) Jang, S. G.; Kramer, E. J.; Hawker, C. J. Controlled Supramolecular Assembly of Micelle-Like Gold Nanoparticles in Ps-B-P2vp Diblock Copolymers Via Hydrogen Bonding. J. Am. Chem. Soc. 2011, 133, 16986-16996.
(33) Frens, G.; Controlled nucleation for the regulation of the particle size in monodisperse gold suspensions, *Nature Phys. Chem.*, 1973, 241, 20.
(34) Schmidt, H. T.; and Ostafin, A. E. *Adv. Mater.*, 2002, 14 (7), 532.
(35) Fernandez-Lopez, C.; Mateo-Mateo, C.; Alvarez-Puebla, R. A.; Perez-Juste, J.; Pastoriza-Santos, I.; Liz-Marzan, L. M. *Langmuir*, 2009, 25 (24), 13894.

Example 2. Concentration-Dependent Association Between Weakly Attractive Nanoparticles in Aqueous Solutions Interactions between nanoparticles in solutions impact many applications including the delivery of nanomedicine, energy transfer between nanoparticles, and the transport of nanomaterials. As described above in Example 1, 100-nm diameter calcium phosphate enclosed liposomes (CaPELs) were used to probe nanoscale energy deposition in CaPELs in the form of X-ray induced energy transfer by 100-nm PEGylated gold nanoparticles (AuNPs) under X-ray irradiation. A jump was observed in the transfer efficiency as AuNP concentration rose above a threshold. In turn, the jump was proposed to be caused by each CaPEL associating with at least one AuNP at high enough AuNP concentrations. In this example, Brownian Dynamics simulations were used to model the interaction between the weakly attractive nanomaterials of AuNPs and CaPELs. For a 6-kcal/mol binding energy between the two, the results presented herein show that AuNPs and CaPELs formed short-lived associations with AuNPs at room temperature in aqueous solutions, and the percentage of CaPELs in these associations jumped sharply to nearly 100% as AuNP concentration rose above a threshold. This agreement between the experimentally observed transfer efficiency trend and that obtained from Brownian Dynamics simulations demonstrated a concentration-dependent, cooperative association between the weakly attractive AuNPs and CaPELs. The trend was also duplicated using existing models such as Klotz or Hill equations with n greater than 3, illustrating a cooperative interaction of these nanomaterials similar to the cooperative binding between ligands and proteins.

Introduction

Nanoparticles interact with each other in solutions. The interactions range from strongly attractive to strongly repulsive. Many important processes rely on the understanding of these interactions. One of the benefits of knowing the interaction dynamics is that it helps lead to an understanding of the self-assembly of nanomaterials (2-7). The dynamics of interactions between nanoparticles are also key to understanding phenomena such as the association, solvation and aggregation of nanoparticles, which are pivotal to understanding drug delivery using nanostructures, the environmental impact of nanomaterials, and theoretical modeling of the behaviors of nanomaterials (8, 9). Understanding the dynamics also reveals how some biomolecules interact with each other and provides deeper insights into designing nanoparticle-based protein mimics (10).

A special category of interaction is between weakly attractive neutral nanomaterials, which is different from interactions between charged nanoparticles that are studied extensively using DLVO theory (11, 12). The weakly attractive nanoparticles have been studied theoretically and behaviors including aggregation or gelation are predicted when these nanoparticles are in "squeezed" conditions such as at high concentrations (5, 13-15). Similar processes also exist in protein solutions at high concentrations, where proteins spontaneously aggregate or self-associate (16-18).

Experimentally it is difficult to study this special type of interaction between nanoparticles in solutions for at least three reasons. First, aggregation only occurs at high densities of nanomaterials, at which point solutions become too dense or opaque to many existing methods such as optical microscopy and transmission electron microscopy (TEM) as well as advanced tools such as dynamic TEM (DTEM) or in situ TEM (19, 20). The second difficulty lies in the fact that the need for nanometer spatial resolution (i.e., to reveal whether there are dimers between nanoparticles) cannot be easily satisfied. Although it is possible to specially prepare samples through freezing and/or dilution to reduce opaqueness and/or stochastic Brownian motion to allow direct imaging and confirmation of dimer formation using optical or electron microscopy, these preparations undoubtedly alter how these species act and may skew or completely change how the nanoparticles interact (21-23). The third difficulty is that the interaction may not cause any optical change even using specially prepared samples. This means that direct visualization is needed. Although it is possible to study the interactions of nanoparticles on substrates with high resolution TEM, the 2D behaviors may be different from 3D behaviors in solutions (24). Therefore, new approaches are needed to help understand the interaction dynamics and validate the theoretical findings mentioned above.

Recently it is demonstrated that X-ray induced energy transfer (XIET, homophone to "excite") may provide the needed high spatial resolution. Such resolution in combination with the highly penetrating power of hard X-rays (20 to 100 keV) make it possible to study nanoparticle interactions at high densities in solutions (see, e.g., Example 1 and (1)). XIET relies on energy transfer between nanomaterial donors and acceptors under X-ray irradiation, and the transfer efficiency depends strongly on the separation between the donors (i.e., X-ray absorbing and electron emitting nanomaterials) and acceptors (i.e., receiving energy deposition from the electrons emitted from the donors). For instance, simulation revealed that the transfer efficiency between 100 nm gold nanoparticle (AuNP) donors and 100 nm diameter, 15-nm thick calcium phosphate (CaP) shell acceptors follows an exponential decay with a 20 nm decay constant as a function of separation between the outer surfaces of the donors and acceptors. In Example 1, it was shown that the transfer efficiency was measured by the reduction of fluorescence yield of sulforhodamine B fluorophores trapped in calcium phosphate shell coated liposomes acceptors, which are called calcium phosphate enclosed liposomes or CaPELs. The XIET efficiency showed a sudden jump at around 0.46 nM of the AuNPs and the jump was attributed to the association between CaPELs and AuNPs at high AuNP concentrations.

Brownian Dynamics (BD) simulations were used in this example to model the interaction between weakly attractive PEGylated AuNP (here called AuNPs) donors and CaPEL acceptors at different AuNP densities. It was found that these AuNPs and CaPELs formed short-lived, transient heterodimers and even trimers, and at high enough AuNP concentrations most of the CaPELs were in the form of heterodimers with AuNPs. The calculated XIET efficiencies using the results from BD simulation matched the experimentally measured transfer efficiencies.

Materials and Methods

Brownian Dynamics (BD) simulations were carried out to study the interaction between PEG-AuNP (here denoted by AuNP unless otherwise noted) and CaPELs. The AuNPs and CaPELs were modeled as hard, 100-nm spheres with a 15-nm layer of calcium phosphate or PEG (25, 26).

BD simulations following the standard protocol reported in the literature were performed with two AuNPs and one CaPEL hard spheres (27). The effective potential energy of the system was described as:

$$U_{eff} = \sum_{i \neq j} U_{i,j}^{rep} + \sum_{\substack{i=AuNP \\ j=CaF}} U_{i,j}^{dim}. \quad \text{(Eq. 1)}$$

Here, the equation:

$$U_{i,j}^{rep} = a_{nb} e^{-b_{nb}(r_{ij}-r_0)}$$

was used to model the repulsive energy between the $i^{th}$ and $j^{th}$ particles at very short distances, where $a_{nb}=10$ kcal/mol, $b_{nb}=0.5$ kcal/mol, $r_0=100$ nm and $r_{ij}$ is the distance between $i^{th}$ and $j^{th}$ particle. Initial simulations showed that $Ca^{2+}$ present on CaPELs attracted PEG on AuNPs, and the attraction force or energy depended on the amount of exposed $Ca^{2+}$ on the surface of CaPELs (28). These initial results were used as the basis for selecting the binding energy used subsequently. Even a relatively small percentage (ca. 5-10%) of exposed $Ca^{2+}$ ions on the surface of 100-nm CaPELs could result in sufficiently strong dispersion forces between the polarizable PEG groups on AuNPs and $Ca^{2+}$ decorated CaPEL particles. Factoring in the detailed molecular events of the association of these nanoparticles, including hydrodynamic interactions, would be required for an accurate atomistic level modeling of the PEG coated-AuNPs and CaPELs, which is not the focus of the current work and was not treated at that level here.

The function:

$$U_{i,j}^{dim} = Ae^{-(r_{ij}-r_{dm})^2/\sigma_{dm}}$$

represents the dimerization free energy between AuNP and CaPEL particles. The parameter $A_{dm}$ was optimized to give a maximum binding free energy of 0, −3, −6 or −12 kcal/mol, while $\sigma_{dm}=10$ nm represents the width of the dimerization potential energy well. The binding free energy was at its minimum at $r_{dm}=130$ nm. The extra distance between the two is assumed to be occupied by the PEG and CaP coating, each of which is about 15 nm.

Further, BD simulations of the 3-particle system were performed within a spherical volume that was constrained using a simple potential:

$$U_{cons} = \Sigma_i P_{cn} e^{Q_{cn}(r_{i,d}-r_{sp})} \quad \text{(Eq. 2)}$$

where, $P_{cn}$=50 kcal/mol, $Q_{cn}$=10 kcal/mol, $r_{i,d}$ is the distance of the $i^{th}$ particle from the center of the sphere and $r_{sp}$ is the effective radius of the simulation sphere.

In order to study the effects of the dimerization energy, four sets of BD simulations were performed, each with values of:

$U_{i,j}^{dim}$=0, −3, −6, or −12 kcal/mol respectively. Each of these four sets of systems with different dimerization potentials were simulated within different spherical volumes, effectively mimicking the experimental conditions of different AuNP concentrations. For example, the simulation sphere with $r_{sp}$=0.5 μm represented an effective AuNP concentration of around 6.4 nM, while those with $r_{sp}$=1.6 μm represented an effective AuNP concentration of around 0.20 nM, respectively.

In order to study the concentration effect on the overall dimerization event, the value:

$U_{i,j}^{dim}$=−6 kcal/mol was chosen. BD simulations were performed by changing $r_{sp}$ from 0.3 μm (corresponding to 30 nM AuNPs) to 2.0 μm, which corresponded to 0.1 nM AuNPs.

BD simulations were performed over the particles of the system by evolving their positions in discrete time steps of Δt=2 ps:

$$R_{i\alpha}(t + \Delta t) = R_{i\alpha}(t) = \beta D_0\left(\frac{\partial U_{eff}}{\partial R_{i\alpha}}\right)\Delta t + A_{R_{i\alpha}}(t) \quad \text{(Eq. 3)}$$

where, $R_{i\alpha}$ is the dimensional coordinate for each $i^{th}$ particle, i runs over the particles and α represents movement in the Cartesian coordinates. Here, the variable:

$A_{R_{i\alpha}}$ is the random displacement that satisfies the fluctuation dissipation relationship and has been extracted from a Gaussian distribution of 0 mean and variance of $2D_0\Delta t$. The parameter $D_0$ represents the short time self-diffusion coefficient and its value was taken as $10^{-8}$, $10^{-9}$ and $10^{-10}$ cm²/sec. Diffusion coefficients less than $10^{-10}$ cm²/sec were not investigated due to much longer times needed to observe converged results.

Using the data obtained from BD simulations, which provided relative positions of two AuNPs and one CaPEL, XIET efficiencies were calculated using a previously developed theoretical program (29). Briefly, the program employing a Monte-Carlo method was used to calculate the energy deposition by electrons emitted from X-ray absorbing AuNPs donors dissolved in water. The electrons include photoelectrons, Auger electrons and Compton electrons. The traditionally defined enhancement of X-ray dose effect or dose enhancement factor as the ratio of the energy deposition in CaPEL acceptors by neighboring AuNP donors at distances to that without AuNPs was used to estimate the transfer efficiency. Absolute XIET efficiency, which is defined as the percentage of energy released from a donor depositing in an acceptor, is difficult to measure, although it can be estimated using theoretical simulations.

The synthesis of the materials were described elsewhere (see, e.g., Example 1 and (1)). AuNPs and CaPELs were synthesized. CaPELs were made in the presence of 1 mM sulforhodamine B (SRB), some of which reacted with radicals generated in water in CaPELs and lost their fluorescence when irradiated with X-rays. Dynamic light scattering (DLS) (Zetasizer Nano S90, Malvern), TEM (JEOL 1230), cryo-TEM (JEOL 2100F) and Nanoparticle Tracking Analysis (NanoSight NS300, Malvern) were used to characterize the samples.

The enhancement measurements were performed with a home-assembled, table-top X-ray instrument using a microfocus X-ray source operated at 100 kVp (30). The X-ray energy was between 20 and 100 keV, emitted from a tungsten target. The samples were irradiated with controls to obtain the enhancement (1). The dose rate was 10 Gy/min and irradiation area was 1.5 cm in diameter. The temperature of the irradiation chamber was monitored and a less than 3° C. temperature change was measured for the duration of the irradiation.

Absorption measurements were made using UV-VIS-NIR spectrophotometers (UV1700 and UV-3600, Shimadzu Scientific Instruments) using short-path low-volume disposable cuvette (SpecVette™, ALine Inc.).

Results and Discussion

A typical BD modeling result is shown in FIG. 17A. The result shows BD modeling using two AuNPs and one CaPEL in a sphere of 0.73 μm radius or 1.46 μm in diameter, which corresponds to 2 nM of AuNPs. The modeling results shown in FIG. 17A reveal BD trajectories for a 50-second period of time and $D_0$ of $10^{-10}$ cm² sec⁻¹. The results show the distances (defined as center-to-center, red (R) and green (G)) between the CaPEL and two AuNPs (red (R) and green (G)), which vary from contacting each other (distance~130 nm) to a maximum allowed distance of 1 μm confined by the spherical boundary condition. The contacting or zero distance is referred to as the "ON" state and greater than zero distance the "OFF" state, which had an average distance greater than 400 nm. The results indicate that for 2 nM AuNP concentration the CaPEL almost always bound to at least one AuNP, and the binding switched between the two AuNPs. This made the CaPEL stay in the "ON" state most of the time. Further, there were periods of time, e.g., between 43 and 48 sec and between 62 and 67 sec, when two AuNPs were in contact with the CaPEL to form a trimer. There were also moments when the CaPEL was away from both AuNPs, e.g., around 69 and 72 sec. The absence of two or more large AuNPs simultaneously attracted to one CaPEL for an extensive period of time was caused by the repulsion or lack of attraction between these AuNPs, as evidenced by the lack of aggregation of large (>15 nm diameter) AuNPs or deposition of multiple large AuNPs on a nanoparticle substrate (31). These results show the transient nature of the heterodimerization process: the heterodimers did not last forever; instead they fell apart automatically as indicated by the departure of the AuNP at 48 (green) and 67 (red) sec shown in FIG. 17.

The overall percentage of the time that the CaPEL and one of the two AuNPs spent as heterodimers was calculated from BD modeling trajectories of 200 seconds for 3 different values of $D_0$, and the results are shown in FIG. 17B. The concentration of AuNPs used to obtain the results shown in FIG. 17A is marked by the arrow/circle in FIG. 17B, at which ~90% of CaPELs were in the heterodimer form. The results shown in FIG. 17B depict the percentage of heterodimer as a function of the radius of the sphere (lower X axis) and AuNP concentration (upper X axis) and the diffusion constant Do. As the radius decreased, the density of AuNPs increased. For all three diffusion coefficients used, the percentages began to rise at around 1.4 μm radius or 0.29 nM. The sharpest rise was obtained using a diffusion coefficient of $10^{-10}$ cm² sec⁻¹ (triangles), which was smaller than literature reported values for 90 nm AuNPs (32). The percentage increased from around 13% at 1.4 μm or 0.29 nM to 68% at 1.2 µm or 0.45 nM and reached 90% at 0.7 µm or 2 nM. For higher diffusion coefficients, the transitions from monomers to heterodimers were more gradual as a function of AuNP concentration.

The dimer percentage curves shown in FIG. 17B can be experimentally verified with XIET measurements. The outcome helps determine how close CaPELs are to AuNPs (1). Assuming that the interaction dynamics follows what FIG. 17 predicts, it is possible to obtain the XIET efficiency by calculating the relative XIET enhancement, which is the enhanced damage to SRB in CaPEL acceptors. The higher the enhancement, the higher the XIET efficiency. The details were shown in recent work (see, e.g., Example 1 and (1)), and predicted XIET efficiencies, i.e., enhancement, as a function of weight percent of gold in water are given in FIG. 18A. As the modeling results suggest, at low concentrations of AuNPs, the dimer percentage was low, and so was the enhancement. A low enhancement value indicated the "OFF" state or a low percentage of heterodimers and a high enhancement value indicated the "ON" state or a high percentage of heterodimers. As the AuNP density rose above a threshold value of 0.29 nM, the enhancement jumped by 2 fold within a 0.1-nM span of AuNP density.

The predicted enhancement can be compared with the experimentally obtained enhancements using the damage to SRB inside CaPELs at different concentrations of AuNPs (1). The results are shown in FIG. 18B, which describes the enhanced reduction of SRB fluorescence in CaPELs with several concentrations of AuNPs, ranging from 0.1 wp to 1.0 wp. At low AuNP concentrations (below 0.2 wp), the enhancement was low and increased as the amount of AuNPs increased at an approximate rate of 1 fold $wp^{-1}$, which was caused by the average physical enhancement (33). The enhancement jumps from 0.56 to 2.7 fold as the concentration increased from 0.2 wp to 0.25 wp AuNPs, which means the enhancement increased by 2.1 fold over a 0.05-wp change in Au in water. The experimental results shown in FIG. 18B qualitatively agree with simulated enhancements caused by heterodimer formation shown in FIG. 18A.

The average sizes of the two weakly attractive nanomaterials CaPELs and AuNPs used in the experiment were 115 nm and 90 nm, respectively, based on TEM inspection. The sizes were larger, 130 and 98 nm if using DLS results. As a result, in modeling a 100 nm size was used for both nanomaterials. When they were mixed and dissolved in aqueous solution, the samples were a thick paste, but without visible aggregation or precipitation. It is possible that the aggregation of AuNPs was not visible to the naked eyes at high concentrations. If this were true, then UV-Vis would show a broadening and shift of the UV-Vis spectra towards the longer wavelength (34). UV-Vis measurements were made using thin micro-cuvettes so that the absorbance was in the measurable and linear range. The samples in Eppendorf tubes are shown in FIG. 19A, samples in the cuvette in FIG. 19B, and the UV-Vis results in FIG. 19C. The results suggest that there was no sudden plasmonic profile change around 0.25 wp for the AuNPs, excluding the possibility of obvious aggregation of AuNPs at 0.25 wp or higher concentrations of AuNPs. The results also confirm that UV-Vis was not sensitive to reveal how AuNPs interact with CaPELs. It is worth pointing out that although NanoSight NS300 was able to detect both CaPELs and AuNPs, the solutions in real samples had to be diluted three orders of magnitude. As a result, optical methods are not suitable for studying the interaction of these nanomaterials.

AuNPs may also precipitate at the end of X-ray exposure, which lasted for about 30 min. This was avoided by shaking and mixing the sample every 8 min. The outcome was the same as other experimental results when samples were not shaken during the X-ray irradiation. AuNPs were also mixed with CaPELs for up to 24 hours prior to irradiation and no difference was observed compared with a 3-hour mixing time. These results show that there was no aggregation between AuNPs during the experiment so that the only dimer formation was the heterodimers discussed above.

The weak attraction between PEG-AuNPs and CaPELs was also confirmed by adding PEG ligands prior to mixing the two nanoparticles; the enhancement jump disappeared after adding PEG ligands first. This is because CaPELs covered with free PEG ligands could no longer interact attractively with AuNPs when free PEG ligands were added to the CaPEL solution before mixing with AuNPs.

The results shown here resemble a special case of protein-ligand interaction process whose outcome can be modeled with the Hill or Klotz equation (35, 36). In such a protein-ligand interaction process, initial ligand binding influences subsequent ligand binding, a process called cooperative binding, which is similar to the phenomenon observed here. At low AuNP concentrations, heterodimers formed and fell apart quickly and most CaPELs stayed single. At high AuNP concentrations the collision interval became shorter than the lifetime of heterodimers, hence each collision between a heterodimer and a AuNP resulted in the formation of a new heterodimer and AuNP. Such collisions perpetuated the existence of heterodimers and the process can be viewed to some degree equivalent to the increased binding of subsequent ligands as the number of ligands bound to protein increases (37). The difference in the heterodimer case is that AuNPs could bind to CaPELs at any location on the surface of CaPELs, although normally only one AuNP binds to a CaPEL due to repulsion between large AuNPs.

Klotz and Hill equations were used to model the binding between AuNPs and CaPELs. For Klotz's model up to three sequential equilibrium steps (i.e., up to n=3) was considered using the generalized Klotz equation (Eq. (7)). The Klotz model is represented as:

$$CaPEL + AuNP \underset{}{\overset{K_1}{\rightleftharpoons}} (CaPEL - AuNP) \tag{Eq. 4}$$

for n=1, $K_1$=0.1-0.01;

$$(CaPEL - AuNP) + AuNP \underset{}{\overset{K_2}{\rightleftharpoons}} (CaPEL - AuNP_2) \tag{Eq. 5}$$

for n=2, $K_1$=1×10$^{-5}$-5×10$^{-5}$ and $K_2$=10-70; and $$(CaPEL - AuNP_2) + AuNP \underset{}{\overset{K_3}{\rightleftharpoons}} (CaPEL - AuNP_3) \tag{Eq. 6}$$

for n=3, $K_1$=1×10$^{-4}$, $K_2$=0.1-0.5, and $K_3$=1-10.

These reaction equations result in a binding fraction or percentage as:

$$\frac{\text{AuNP bound CaPEL sites}}{\text{Total sites on CaPEL}} = \qquad (Eq.\ 7)$$

$$\frac{1}{n}\left(\frac{K_1[AuNP] + 2K_1K_2([AuNP]^2) + \ldots + n(K_1K_2\ldots K_n)[AuNP]^n}{1 + K_1[AuNP] + K_1K_2([AuNP]^2) + \ldots + (K_1K_2\ldots K_n)[AuNP]^n}\right)$$

In case of Hill equation (Eq. (9)) a Hill coefficient of four (i.e., n=4) or greater was needed, suggesting a strong cooperative binding phenomenon. The Hill reaction is represented as:

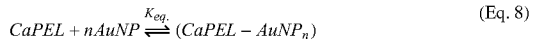
(Eq. 8)

resulting in a binding fraction of:

$$\frac{\text{AuNP bound CaPEL sites}}{\text{Total sites on CaPEL}} = \frac{[AuNP]^n}{[AuNP]^n + K_d} \qquad (Eq.\ 9)$$

where, $K_d=1/K_{eq}$ and in the fitting n=4±0.4 and $K_d=1\times10^{-5}$-$5\times10^{-5}$ were used.

FIG. 20 shows the results of modeling the binding for n up to 3 for the Klotz and n=4 for the Hill equation. FIG. 20A shows the individual cases of n=1, 2 and 3 for the Klotz equation. It is evident that n=1 clearly does not duplicate the experimentally observed dimer fraction trend. n=2 case begins to resemble the experimental trend. Also shown in FIG. 20A is the simulated binding percentage for n=4 for the Hill equation. FIG. 20B shows the comparison between the experimental transfer efficiency data in terms of enhancement and the calculated enhancements. The result for n=1 (Klotz) is not shown here because clearly it cannot be used to explain the experimental results. The best match was the result of binding percentages modeled using the Klotz equation with n=3 and optimized equilibrium constants $K_1$, $K_2$ and $K_3$. Although up to n=3 in the Klotz modeling is done here, it is expected that higher n will produce a better matching between the fitting and the experimental data. On the other hand, the Hill equation with even n=4 did not yield satisfactory results.

Figure 21:
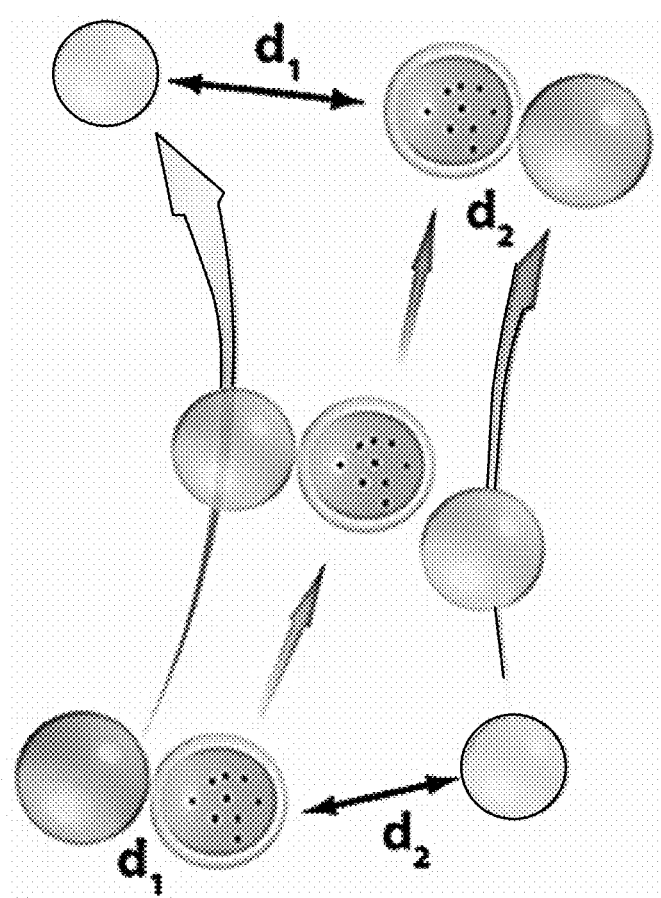
FIG. 21 illustrates how a CaPEL interacts with AuNPs in solution. A heterodimer ($d_1$) has a finite lifetime. If the concentration of AuNPs is high enough, then a collision between an AuNP and a heterodimer ($d_1$) would lead to the formation of another heterodimer ($d_2$), perpetuating the existence of heterodimer as far as XIET is concerned.
Figure 22:
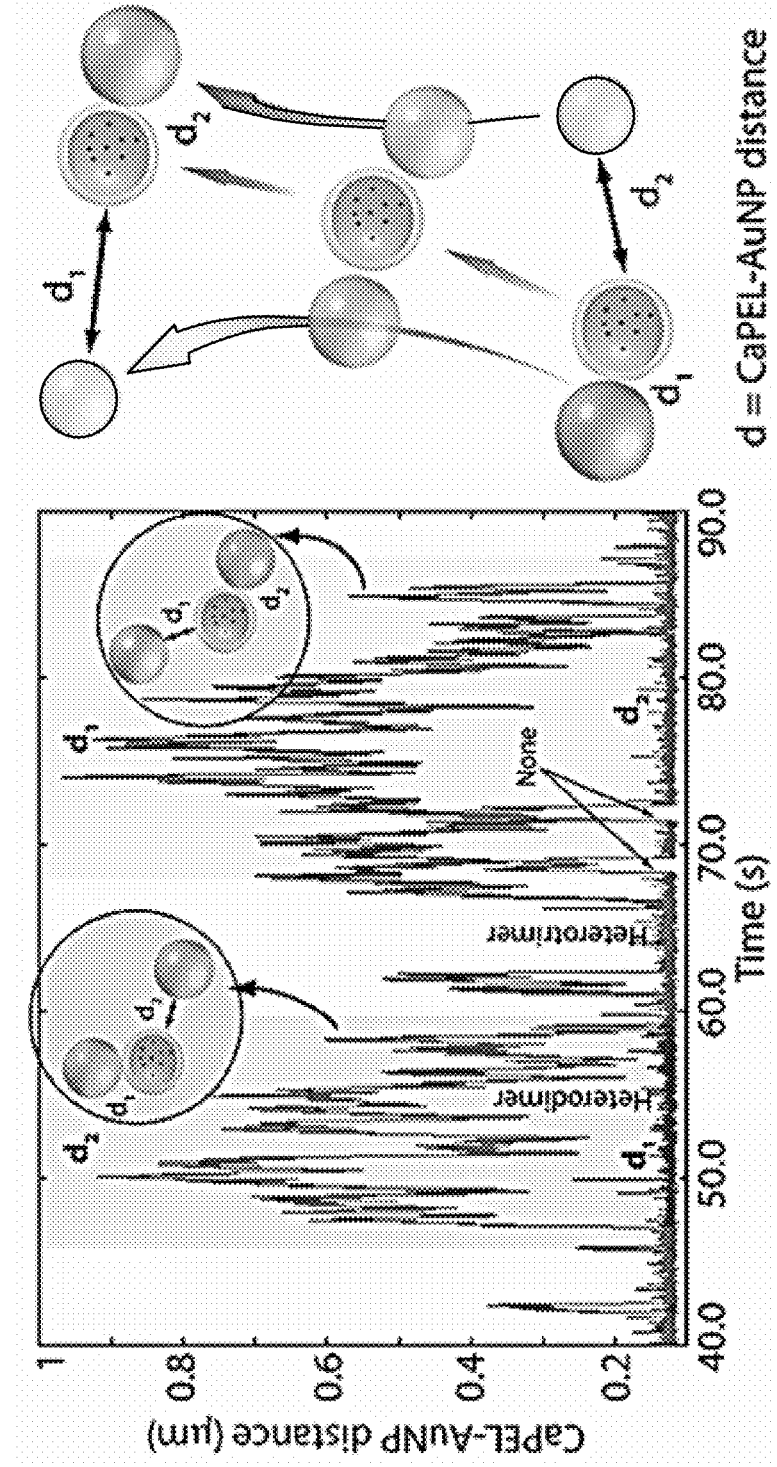
FIG. 22 depicts interactions between CaPELs and AuNPs.

FIG. 21 summarizes the association processes demonstrated study in which a CaPEL binds to one AuNP for some time and then switches to another AuNP. The length of time the CaPEL shown in the FIG. 21 spent with one AuNP depended on the binding energy, the frequency of collision, and the concentration of AuNPs.

The magnitude of attraction was estimated to be approximately 6 kcal/mol. This relatively weak force explains why the heterodimers did not stay together for a long time. The best match between BD and XIET results suggest that the diffusion coefficients for 100 nm AuNPs was lower than the literature reported values. This may be attributed to the high concentration AuNPs used here. It has been reported that the diffusion coefficient may be dependent of nanoparticle concentrations (38), although insufficient data is available especially under the current experimental condition to ascertain such dependence.

In this work the relative efficiency of XIET was used to infer the existence of heterodimers because the transfer efficiency dropped to nearly zero when the separation (defined as distance between outer surfaces) between the donors and acceptors was 20-50 nm. This spatial resolution may be improved further by synthesizing and employing smaller sized nanoscale acceptors. Such a resolution is adequate to study whether a nanoscale probe binds directly to a target in hidden space. Because X-rays of 100 keV are highly penetrating, interactions in high density, opaque samples may be studied.

It is also possible to use pulsed X-rays to perform time-resolved measurements and therefore increase the temporal resolution. The dose requirement shown here is high, of the order of 1 kGy, which is available from many pulsed X-ray sources (39-41). Pulsed X-rays make it possible to study dynamics of nanomaterial interactions in hidden space such as in the environment, body and animals.

Conclusion

The results presented here demonstrate that X-ray induced energy transfer is useful for investigating hard-to-access dynamics with nanometer resolution. The combination of experimental and theoretical studies made it possible to obtain the dynamics as well as the binding energy between weakly attractive nanoparticles. The latter was found to be approximately 6 kcal/mol between PEGylated gold nanoparticles and calcium phosphate enclosed liposomes. The heterodimers formed between the two nanoparticles were predicted to be short-lived or transient, falling apart automatically at room temperature. The existence of heterodimers and the resulting XIET efficiency, however, was found to be dependent of the concentration of gold nanoparticles because the binding can be cooperative, meaning that CaPELs may stay in formation of heterodimers if there are enough gold nanoparticles around them. The collisions, if frequent enough, between gold nanoparticles and heterodimers may result in the formation of other heterodimers, effectively perpetuating the existence of heterodimers and leading to the energy transfer efficiency jump.

REFERENCES (1) Sharmah, A.; Yao, Z.; Lu, L.; Guo, T. X-Ray-Induced Energy Transfer between Nanomaterials under X-Ray Irradiation. *J. Phys. Chem. C* 2016, 120, 3054-3060.
(2) Meng, G. N.; Arkus, N.; Brenner, M. P.; Manoharan, V. N. The Free-Energy Landscape of Clusters of Attractive Hard Spheres. *Science* 2010, 327, 560-563.
(3) Odriozola, G.; Schmitt, A.; Moncho-Jorda, A.; Callejas-Femandez, J.; Martinez-Garcia, R.; Leone, R.; Hidalgo-Alvarez, R. Constant Bond Breakup Probability Model for Reversible Aggregation Processes. *Phys Rev E* 2002, 65.
(4) Min, Y. J.; Akbulut, M.; Kristiansen, K.; Golan, Y.; Israelachvili, J. The Role of Interparticle and External Forces in Nanoparticle Assembly. *Nat. Mater.* 2008, 7, 527-538.
(5) Whitmer, J. K.; Luijten, E. Influence of Hydrodynamics on Cluster Formation in Colloid-Polymer Mixtures. *J. Phys. Chem. B* 2011, 115, 7294-7300.
(6) Wang, L. B.; Xu, L. G.; Kuang, H.; Xu, C. L.; Kotov, N. A. Dynamic Nanoparticle Assemblies. *Acc. Chem. Res.* 2012, 45, 1916-1926.
(7) Love, J. C.; Estroff, L. A.; Kriebel, J. K.; Nuzzo, R. G.; Whitesides, G. M. Self-Assembled Monolayers of Thiolates on Metals as a Form of Nanotechnology. *Chem. Rev.* 2005, 105, 1103-1169.

(8) Murthy, A. K.; Stover, R. J.; Borwankar, A. U.; Nie, G. D.; Gourisankar, S.; Truskett, T. M.; Sokolov, K. V.; Johnston, K. P. Equilibrium Gold Nanoclusters Quenched with Biodegradable Polymers. *ACS Nano* 2013, 7, 239-251.

(9) Alsharif, S. A.; Chen, L. Y.; Tlahuice-Flores, A.; Whetten, R. L.; Yacaman, M. J. Interaction between Functionalized Gold Nanoparticles in Physiological Saline. *Phys. Chem. Chem. Phys.* 2014, 16, 3909-3913.

(10) Kotov, N. A. Inorganic Nanoparticles as Protein Mimics. *Science* 2010, 330, 188-189.

(11) Zaccone, A.; Gentili, D.; Wu, H.; Morbidelli, M. Shear-Induced Reaction-Limited Aggregation Kinetics of Brownian Particles at Arbitrary Concentrations. *J. Chem. Phys.* 2010, 132.

(12) Westermeier, F.; Fischer, B.; Roseker, W.; Grubel, G.; Nagele, G.; Heinen, M. Structure and Short-Time Dynamics in Concentrated Suspensions of Charged Colloids. *J. Chem. Phys.* 2012, 137.

(13) Kovalchuk, N. M.; Starov, V. M. Aggregation in Colloidal Suspensions: Effect of Colloidal Forces and Hydrodynamic Interactions. *Adv. Colloid Interface Sci.* 2012, 179, 99-106.

(14) Olivier, B. J.; Sorensen, C. M. Variable Aggregation Rates in Colloidal Gold-Kernel Homogeneity Dependence on Aggregant Concentration. *Phys. Rev. A* 1990, 41, 2093-2100.

(15) Arkus, N.; Manoharan, V. N.; Brenner, M. P. Minimal Energy Clusters of Hard Spheres with Short Range Attractions. *Phys. Rev. Lett.* 2009, 103.

(16) Wang, W.; Xu, W. X.; Levy, Y.; Trizac, E.; Wolynes, P. G. Confinement Effects on the Kinetics and Thermodynamics of Protein Dimerization. *Proc. Natl. Acad. Sci. U.S.A.* 2009, 106, 5517-5522.

(17) Shire, S. J.; Shahrokh, Z.; Liu, J. Challenges in the Development of High Protein Concentration Formulations. *J. Pharm. Sci.* 2004, 93, 1390-1402.

(18) Sule, S. V.; Sukumar, M.; Weiss, W. F.; Marcelino-Cruz, A. M.; Sample, T.; Tessier, P. M. High-Throughput Analysis of Concentration-Dependent Antibody Self-Association. *Biophys. J.* 2011, 101, 1749-1757.

(19) Barwick, B.; Park, H. S.; Kwon, O. H.; Baskin, J. S.; Zewail, A. H. 4D Imaging of Transient Structures and Morphologies in Ultrafast Electron Microscopy. *Science* 2008, 322, 1227-1231.

(20) Lorenz, U. J.; Zewail, A. H. Observing Liquid Flow in Nanotubes by 4d Electron Microscopy. *Science* 2014, 344, 1496-1500.

(21) Cerbelaud, M.; Ferrando, R.; Videcoq, A. Simulations of Heteroaggregation in a Suspension of Alumina and Silica Particles: Effect of Dilution. *J. Chem. Phys.* 2010, 132.

(22) Bhattacharya, S.; Narasimha, S.; Roy, A.; Banerjee, S. Does Shining Light on Gold Colloids Influence Aggregation? *Sci Rep—UK* 2014, 4.

(23) Baalousha, M. Aggregation and Disaggregation of Iron Oxide Nanoparticles: Influence of Particle Concentration, pH and Natural Organic Matter. *Sci. Total Environ.* 2009, 407, 2093-2101.

(24) Li, D. S.; Nielsen, M. H.; Lee, J. R. I.; Frandsen, C.; Banfield, J. F.; De Yoreo, J. J. Direction-Specific Interactions Control Crystal Growth by Oriented *Attachment. Science* 2012, 336, 1014-1018.

(25) Hong, B. B.; Panagiotopoulos, A. Z. Molecular Dynamics Simulations of Silica Nanoparticles Grafted with Poly (Ethylene Oxide) Oligomer Chains. *J. Phys. Chem. B* 2012, 116, 2385-2395.

(26) Khan, S. J.; Pierce, F.; Sorensen, C. M.; Chakrabarti, A. Self-Assembly of Ligated Gold Nanoparticles: Phenomenological Modeling and Computer Simulations. *Langmuir* 2009, 25, 13861-13868.

(27) Ermak, D. L.; Mccammon, J. A. Brownian Dynamics with Hydrodynamic Interactions. *J. Chem. Phys.* 1978, 69, 1352-1360.

(28) Okada, T. Efficient Evaluation of Poly(Oxyethylene) Complex-Formation with Alkali-Metal Cations. *Macromolecules* 1990, 23, 4216-4219.

(29) Lee, C.; Cheng, N. N.; Davidson, R. A.; Guo, T. Geometry Enhancement of Nanoscale Energy Deposition by X-Rays. *J. Phys. Chem. C* 2012, 116, 11292-11297.

(30) Cheng, N. N.; Starkewolf, Z.; Davidson, A. R.; Sharmah, A.; Lee, C.; Lien, J.; Guo, T. Chemical Enhancement by Nanomaterials under X-Ray Irradiation. *J. Am. Chem. Soc. Commun.* 2012, 134, 1950-1953 1950.

(31) Gschneidtner, T. A.; Fernandez, Y. A. D.; Syrenova, S.; Westerlund, F.; Langhammer, C.; Moth-Poulsen, K. A Versatile Self-Assembly Strategy for the Synthesis of Shape-Selected Colloidal Noble Metal Nanoparticle Heterodimers. *Langmuir* 2014, 30, 3041-3050.

(32) Albaladejo, S.; Marques, M. I.; Scheffold, F.; Saenz, J. J. Giant Enhanced Diffusion of Gold Nanoparticles in Optical Vortex Fields. *Nano Lett.* 2009, 9, 3527-3531.

(33) Davidson, R. A.; Guo, T. Average Physical Enhancement by Nanomaterials under X-Ray Irradiation. *J. Phys. Chem. C* 2014, 118, 30221-30228.

(34) Cheng, Y. N.; Wang, M.; Borghs, G.; Chen, H. Z. Gold Nanoparticle Dimers for Plasmon Sensing. *Langmuir* 2011, 27, 7884-7891.

(35) Klotz, I. M. The Application of the Law of Mass Action to Binding by Proteins—Interactions with Calcium. *Arch Biochem* 1946, 9, 109-117.

(36) Bindslev, N. *Drug-Acceptor Interactions*; Co-Action Publishing, 2008.

(37) Klotz, I. M. Ligand-Receptor Complexes: Origin and Development of the Concept. *J. Biol. Chem.* 2004, 279, 1-12.

(38) Nestle, N. F. E. I.; Kimmich, R. Concentration-Dependent Diffusion Coefficients and Sorption Isotherms. Application to Ion Exchange Processes as an Example. *J Phys. Chem.* 1996, 100, 12569-12573.

(39) Penfold, T. J.; Milne, C. J.; Chergui, M. Recent Advances in Ultrafast X-Ray Absorption Spectroscopy of Solutions. *Advances in Chemical Physics, Vol* 153 2013, 153, 1-41.

(40) Hada, M.; Matsuo, J. Ultrafast X-Ray Sources for Time-Resolved Measurements. *X-Ray Spectrom.* 2012, 41, 188-194.

(41) Wenz, J.; Schleede, S.; Khrennikov, K.; Bech, M.; Thibault, P.; Heigoldt, M.; Pfeiffer, F.; Karsch, S. Quantitative X-Ray Phase-Contrast Microtomography from a Compact Laser-Driven Betatron Source. *Nat. Commun.* 2015, 6.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

What is claimed is:

1. A method of confirming a targeting operation, the method comprising:
    delivering a donor material to a target;
    delivering a probe to the target, wherein the probe couples with the donor material;
    irradiating the target;
    determining an optical change in the probe to confirm the donor material and probe reached the target;
    delivering a solution to dislodge the probe from the donor material; and
    extracting the probe from the target, wherein the target is in a living organism.

2. The method of claim 1, further comprising:
    functionalizing the donor material to seek the target; and
    functionalizing the probe to conjugate with the donor material.

3. The method of claim 1, wherein the target comprises cancerous tissue in the living organism, and wherein extracting the probe comprises a blood draw.

4. The method of claim 1, wherein the solution comprises a pH of within a range of 8.0-8.5, and wherein the solution severs the coupling between the probe and the donor material.

5. The method of claim 1, wherein the probe comprises dye molecules, and wherein determining an optical change in the probe comprises detecting destruction of the dye molecules.

6. The method of claim 1, wherein the donor material comprises at least one material selected from the group consisting of lanthanide oxide, hafnium oxide, tungsten oxide, platinum, gold, bismuth, and uranium-238.

7. The method of claim 6, wherein the donor material comprises a nanomaterial having a diameter between about 25 nm and about 1,000 nm.

8. The method of claim 1, wherein the probe comprises at least one material selected from the group consisting of $TiO_2$, ZnO, $Al_2O_3$, $SiO_2$, CaP, polystyrene, and poly N-isopropylacrylamide.

9. The method of claim 8, wherein the probe further comprises at least one material selected from the group consisting of coumarin-3-carboxylic acid, 3'-(p aminophenyl) fluorescein, 2-[6-(4V-amino)phenoxy-3H-xanthen-3-on-9-yl] benzoic acid (APF), dihydroethidine (DHE), dihydrorhodamine, 4',5'-diaminofluorescein, sulforhodamine B, calcein, and fluorescein.

10. The method of claim 8, wherein the probe is characterized by a diameter of between about 2 nm and about 500 nm.

11. The method of claim 10, wherein the probe is characterized by a diameter of between about 5 nm and about 100 nm.

12. A method of determining conjugation between a probe nanomaterial and a donor nanomaterial, the method comprising:
    functionalizing a donor nanomaterial to target a substance, wherein the donor nanomaterial comprises at least one material selected from the group consisting of lanthanide oxide, hafnium oxide, tungsten oxide, platinum, gold, bismuth, and uranium-238, and wherein the donor nanomaterial comprises a nanomaterial having a diameter between about 25 nm and about 1,000 nm;
    delivering the donor nanomaterial to a location;
    functionalizing a probe nanomaterial to target the donor nanomaterial;
    delivering the probe nanomaterial to the location;
    irradiating the location with radiation from a source selected from the group consisting of an X-ray source, a microwave source, or a gamma ray source;
    testing the probe nanomaterial to identify a change in optical characteristics;
    determining successful conjugation between the probe nanomaterial and the donor nanomaterial at the location; and based on determining successful conjugation, determining the substance exists at the location.

13. The method of claim 12, wherein the probe nanomaterial comprises at least one material selected from the group consisting of $TiO_2$, ZnO, $Al_2O_3$, $SiO_2$, CaP, polystyrene, and poly N-isopropylacrylamide.

14. The method of claim 13, wherein the probe nanomaterial further comprises at least one material selected from the group consisting of coumarin-3-carboxylic acid, 3-(p aminophenyl) fluorescein, 2-[6-(4V-amino)phenoxy-3H-xanthen-3-on-9-yl] benzoic acid (APF), dihydroethidine (DHE), dihydrorhodamine, 4',5'-diaminofluorescein, sulforhodamine B, calcein, and fluorescein.

15. The method of claim 13, wherein the probe nanomaterial is characterized by a diameter of between about 2 nm and about 500 nm.

16. The method of claim 15, wherein the probe nanomaterial is characterized by a diameter of between about 5 nm and about 100 nm.

17. A method of confirming a targeting operation, the method comprising:
    delivering a donor material to a target;
    delivering a probe to the target, wherein the probe comprises at least one material selected from the group consisting of $TiO_2$, ZnO, $Al_2O_3$, $SiO_2$, CaP, polystyrene, and poly N-isopropylacrylamide, wherein the probe further comprises at least one material selected from the group consisting of coumarin-3-carboxylic acid, 3'-(p aminophenyl) fluorescein, 2-[6-(4V-amino)phenoxy-3H-xanthen-3-on-9-yl] benzoic acid (APF), dihydroethidine (DHE), dihydrorhodamine, 4',5'-diaminofluorescein, sulforhodamine B, calcein, and fluorescein, and wherein the probe is characterized by a diameter of between about 2 nm and about 500 nm;
    irradiating the target with radiation from a source selected from the group consisting of an X-ray source, a microwave source, or a gamma ray source; and
    determining an optical change in the probe to confirm the donor material and probe reached the target.

18. The method of claim 17, wherein the donor material comprises at least one material selected from the group consisting of lanthanide oxide, hafnium oxide, tungsten oxide, platinum, gold, bismuth, and uranium-238.

19. The method of claim 12, further comprising:
    delivering a solution to dislodge the probe from the donor nanomaterial.

20. The method of claim 19, further comprising:
    extracting the probe from the location.

* * * * *